US009816990B2

(12) United States Patent
Geddes

(10) Patent No.: US 9,816,990 B2
(45) Date of Patent: Nov. 14, 2017

(54) ULTRA-FAST PATHOGEN TOXIN DETECTION ASSAY BASED ON MICROWAVE-ACCELERATED METAL-ENHANCED FLUORESCENCE

(71) Applicant: UNIVERSITY OF MARYLAND, BALTIMORE COUNTY, Baltimore, MD (US)

(72) Inventor: Chris D. Geddes, Bel-Air, MD (US)

(73) Assignee: UNIVERSITY OF MARYLAND, BALTIMORE COUNTY, Baltimore, MD (US)

( * ) Notice: Subject to any disclaimer, the term of this patent is extended or adjusted under 35 U.S.C. 154(b) by 733 days.

(21) Appl. No.: 14/187,789

(22) Filed: Feb. 24, 2014

(65) Prior Publication Data

US 2014/0242604 A1    Aug. 28, 2014

Related U.S. Application Data

(60) Provisional application No. 61/770,380, filed on Feb. 28, 2013.

(51) Int. Cl.
*G01N 33/543* (2006.01)
*G01N 33/569* (2006.01)
(Continued)

(52) U.S. Cl.
CPC ......... *G01N 33/56911* (2013.01); *C12Q 1/04* (2013.01); *G01N 33/54313* (2013.01); *G01N 33/54373* (2013.01); *G01N 33/582* (2013.01); *G01N 2333/32* (2013.01); *G01N 2500/00* (2013.01)

(58) Field of Classification Search
None
See application file for complete search history.

(56) References Cited

U.S. PATENT DOCUMENTS 7,095,502 B2    8/2006    Lakowicz et al.
7,400,397 B2    7/2008    Lakowicz et al.
(Continued)

FOREIGN PATENT DOCUMENTS

WO    WO2004024191    3/2004
WO    WO2012129150    9/2012

OTHER PUBLICATIONS

Albrecht, M.T. et al. Human monoclonal antibodies against anthrax lethal factor and protective antigen act independently to protect against *Bacillus anthracis* infection and enhance endogenous immunity to anthrax, *Infect. Immun.*, 75 (2007), pp. 5425-5433.
(Continued)

*Primary Examiner* — Rebecca Martinez
(74) *Attorney, Agent, or Firm* — Tristan A. Fuierer; Marianne Fuierer; Moore & Van Allen, PLLC

(57) ABSTRACT

The present invention provides for a system and method to detect low levels of the anthrax protective antigen (PA) exotoxin in biological fluids, wherein the system uses a metal-enhanced fluorescence (MEF)-PA assay in combination with microwave-accelerated PA protein surface absorption. Microwave irradiation rapidly accelerates PA deposition onto the surface adjacent to deposited metallic particles and significantly speeding up the MEF-PA assay and resulting in a total assay run time of less than 40 min with an analytical sensitivity of less than 1 pg/ml PA.

8 Claims, 11 Drawing Sheets

(51) Int. Cl.
    C12Q 1/04      (2006.01)
    G01N 33/58     (2006.01)

(56) References Cited

U.S. PATENT DOCUMENTS

| | | | |
|---|---|---|---|
| 7,566,783 | B2 | 7/2009 | Lakowicz |
| 7,718,804 | B2 | 5/2010 | Geddes et al. |
| 7,732,215 | B2 | 6/2010 | Geddes et al. |
| 7,776,528 | B2 | 8/2010 | Lakowicz |
| 7,939,333 | B2 | 5/2011 | Geddes et al. |
| 7,989,220 | B2 | 8/2011 | Lakowicz et al. |
| 8,008,067 | B2 | 8/2011 | Geddes et al. |
| 8,027,039 | B2 | 9/2011 | Lakowicz et al. |
| 8,034,633 | B2 | 10/2011 | Geddes |
| 8,075,956 | B2 | 12/2011 | Geddes et al. |
| 8,101,424 | B2 | 1/2012 | Geddes |
| 8,114,598 | B2 | 2/2012 | Geddes et al. |
| 8,182,878 | B2 | 5/2012 | Geddes et al. |
| 8,318,087 | B2 | 11/2012 | Geddes |
| 8,338,602 | B2 | 12/2012 | Geddes et al. |
| 8,404,450 | B2 | 3/2013 | Geddes |
| 8,569,502 | B2 | 10/2013 | Geddes et al. |
| 8,618,505 | B2 | 12/2013 | Geddes |
| 8,679,402 | B2 | 3/2014 | Geddes |
| 8,679,855 | B2 | 3/2014 | Geddes |
| 8,722,428 | B2 | 5/2014 | Geddes |
| 8,735,175 | B2 | 5/2014 | Geddes |
| 8,759,110 | B2 | 6/2014 | Geddes |
| 2003/0228682 | A1 | 12/2003 | Lakowicz |
| 2006/0256331 | A1 | 11/2006 | Geddes |
| 2007/0269826 | A1 | 11/2007 | Geddes |
| 2008/0215122 | A1 | 9/2008 | Geddes |
| 2009/0022766 | A1 | 1/2009 | Geddes |
| 2009/0325199 | A1 | 12/2009 | Geddes |
| 2011/0020946 | A1 | 1/2011 | Geddes |
| 2011/0207236 | A1 | 8/2011 | Geddes |
| 2012/0021443 | A1 | 1/2012 | Geddes |
| 2012/0028270 | A1 | 2/2012 | Geddes |
| 2012/0107952 | A1 | 5/2012 | Geddes |
| 2012/0282630 | A1 | 11/2012 | Geddes |
| 2013/0115710 | A1 | 5/2013 | Geddes |
| 2013/0156938 | A1 | 6/2013 | Geddes |
| 2014/0030700 | A1 | 1/2014 | Geddes |

OTHER PUBLICATIONS

Aslan, K. et al. Microwave-accelerated metal-enhanced fluorescence. Platform technology for ultrafast and ultrabright assays, *Anal. Chem.*, 77 (2005), pp. 8057-8067.
Aslan, K. et al. Metal-enhanced fluorescence. An emerging tool in biotechnology, *Curr. Opin. Biotechnol.*, 16 (2005), pp. 55-62.
Aslan, K. et al. Microwave-accelerated metal-enhanced fluorescence (MAMEF): application to ultra fast and sensitive clinical assays, *J. Fluoresc.*, 16 (2006), pp. 3-8.
Aslan, K. et al. Microwave-accelerated metal-enhanced fluorescence (MAMEF) with silver colloids in 96-well plates: application to ultra fast and sensitive immunoassays, high throughput screening, and drug discovery, *J. Immunol. Methods*, 312 (2006), pp. 137-147.
Aslan, K. et al. Metal-enhanced fluorescence-based RNA sensing, *J. Am. Chem. Soc.*, 128 (2006), pp. 4206-4207.
Aslan, K. et al. Microwave-accelerated metal-enhanced fluorescence. Application to detection of genomic and exosporium anthrax DNA in <30 s, *Analyst*, 132 (2007), pp. 1130-1138.
Aslan, K. et al. New tools for rapid clinical and bioagent diagnostics: microwaves and plasmonic nano structures, *Analyst*, 133 (2008), pp. 1469-1480.
Biagini, R.E. et al. Determination of serum IgG antibodies to *Bacillus anthracis* protective antigen in environmental sampling workers using a fluorescent covalent microsphere immunoassay, *Occup. Environ. Med.*, 61 (2004), pp. 703-708.
Boyer, A. E. et al. Quantitative mass spectrometry for bacterial protein toxins: a sensitive, specific, high-throughput tool for detection and diagnosis, *Molecules*, 16 (2011), pp. 2391-2413.

Brachman, P.S. Inhalation anthrax, *Ann. N.Y. Acad. Sci.*, 353 (1980), pp. 83-93.
Brittingham, K.C. et al. Dendritic cells endocytose *Bacillus anthracis* spores: implications for anthrax pathogenesis, *J. Immunol.*, 174 (2005), pp. 5545-5552.
Cleret, A. et al. Lung dendritic cells rapidly mediate anthrax spore entry through the pulmonary route, *J. Immunol.*, 178 (2007), pp. 7994-8001.
Cummings, R.T. et al. A peptide-based fluorescence resonance energy transfer assay for *Bacillus anthracis* lethal factor protease, Proc. Natl. Acad. Sci. USA, 99 (2002), pp. 6603-6606.
Dixon, T.C. et al. Anthrax, *N. Engl. J. Med.*, 341 (1999), pp. 815-826.
Dragan, A.I. et al. Two-color, 30-second microwave-accelerated metal-enhanced fluorescence DNA assays: a new rapid catch and signal (RCS) technology, *J. Immunol. Methods*, 366 (2011), pp. 1-7.
Dragan, A.I. et al. Excitation volumetric effects (EVE) in metal-enhanced fluorescence, *Phys. Chem. Chem. Phys.*, 13 (2011), pp. 3831-3838.
Edwards, K. A. et al. *Bacillus anthracis*: toxicology, epidemiology, and current rapid-detection methods, *Anal. Bioanal. Chem.*, 384 (2006), pp. 73-84.
Frank, R. et al. Clinical biomarkers in drug discovery and development, *Nat. Rev. Drug Discovery*, 2 (2003), pp. 566-580.
Geddes, C.D. et al. Metal-enhanced fluorescence, *J. Fluoresc.*, 12 (2002), pp. 121-129.
Guidi-Rontani, C. et al. Fate of germinated *Bacillus anthracis* spores in primary murine macrophages, *Mol. Microbiol.*, 42 (2001), pp. 931-938.
Huan, T.N. et al. Sensitive detection of an anthrax biomarker using a glassy carbon electrode with a consecutively immobilized layer of polyaniline/carbon nanotube/peptide, *Biosens. Bioelectron.*, 26 (2011), pp. 4227-4230.
He, Y. et al. Bioinformatics analysis of bacterial protective antigens in manually curated Protegen database. *Procedia in Vaccinology*. 2012. vol. 6. pp. 3-9.
Huang, R.P. Detection of multiple proteins in an antibody-based protein microarray system, *J. Immunol. Methods*, 255 (2001), pp. 1-13.
Jernigan, J.A. et al. Bioterrorism-related inhalational anthrax: the first 10 cases reported in the United States, *Emerg. Infect. Dis.*, 7 (2001), pp. 933-944.
Klimpel, K.R. et al. Anthrax toxin protective antigen is activated by a cell surface protease with the sequence specificity and catalytic properties of furin, *Proc. Natl. Acad. Sci. USA*, 89 (1992), pp. 10277-10281.
Kobiler, D. et al. Protective antigen as a correlative marker for anthrax in animal models, *Infect. Immun.*, 74 (2006), pp. 5871-5876.
Mabry, R. et al. Detection of anthrax toxin in the serum of animals infected with *Bacillus anthracis* by using engineered immunoassays, *Clin. Vaccine Immunol.*, 13 (2006), pp. 671-677.
Milne, J.C. et al. Anthrax protective antigen forms oligomers during intoxication of mammalian cells, *J. Biol. Chem.*, 269 (1994), pp. 20607-20612.
Moayeri, M. et al. Anthrax protective antigen cleavage and clearance from the blood of mice and rats, *Infect. Immun.*, 75 (2007), pp. 5175-5184.
Mogridge, J. et al. Stoichiometry of anthrax toxin complexes, *Biochemistry*, 41 (2002), pp. 1079-1082.
Mogridge, J. et al. The lethal and edema factors of anthrax toxin bind only to oligomeric forms of the protective antigen, *Proc. Natl. Acad. Sci. USA*, 99 (2002), pp. 7045-7048.
Pribik, R. et al. Metal-enhanced fluorescence (MEF): physical characterization of silver island films and exploring sample geometries, *Chem. Phys. Lett.*, 478 (2009), pp. 70-74.
Ross, J.M. The pathogenesis of anthrax following the administration of spores by the respiratory route, *J. Pathol. Bacteriol.*, 73 (1957), pp. 485-494.
Smith, H. et al. Observations on experimental anthrax: demonstration of a specific lethal factor produced in vivo by *Bacillus anthracis*, *Nature*, 173 (1954), pp. 869-870.

(56) References Cited

OTHER PUBLICATIONS

Smith, H. et al. The chemical basis of the virulence of Bacillus anthracis: IV. Secondary shock as the major factor in death of guinea pigs from anthrax, *Br. J. Exp. Pathol.*, 36 (1955), pp. 323-335.
Swanson, E.R. et al. Anthrax threats: a report of two incidents from Salt Lake City, *J. Emerg. Med.*, 18 (2000), pp. 229-232.
Swartz, M.N. Recognition and management of anthrax—an update, *N. Engl. J. Med.*, 345 (2001), pp. 1621-1626.
Tang, S. et al. Detection of anthrax toxin by an ultrasensitive immunoassay using europium nanoparticles, *Clin. Vaccine Immunol.*, 16 (2009), pp. 408-413.
Walsh, J.J. et al. A case of naturally acquired inhalation anthrax: clinical care and analyses of anti-protective antigen immunoglobulin G and lethal factor, *Clin. Infect. Dis.*, 44 (2007), pp. 968-971.
Yang, B. et al. Protegen: a web-based protective antigen database and analysis system. *Nucleic Acids Research*. 2011, vol. 39, Database issue D1073-D1078.

ULTRA-FAST PATHOGEN TOXIN DETECTION ASSAY BASED ON MICROWAVE-ACCELERATED METAL-ENHANCED FLUORESCENCE

CROSS-REFERENCE TO RELATED TO APPLICATION

The present application claims priority to U.S. Provisional Patent Application No. 61/770,380 filed on Feb. 28, 2013 the contents of which are hereby incorporated by reference herein for all purposes.

BACKGROUND OF THE INVENTION

Technical Field

The present invention relates to assays and methods of use, and more particularly, to detection of protective antigens (PA) during presymptomatic infection to eliminate the need for multiple diagnostic tests and enables early therapeutic intervention.

Related Art

Rapid presymptomatic diagnosis of Bacillus anthracis at early stages of infection plays a crucial role in prompt medical intervention to prevent rapid disease progression and accumulation of lethal levels of toxin. Bacterial infection typically alters the host's homeostasis triggering perturbations to various cellular and molecular networks. Biomarkers indicative of this altered condition can be either pathogen- or host-derived. Common targets include measurable genes, proteins, metabolites, and other indicators associated with immunological, pathological, and/or clinical outcomes [1]. Rapid detection of these biomarkers at early stages of infection increases the chances of an accurate diagnosis when the patient is presymptomatic, and successful medical intervention can be initiated. This is particularly critical for the treatment of Bacillus anthracis, the etiological bacterium of anthrax, which is often difficult to diagnose and spreads rapidly in the patient.

Clinically, anthrax presents with three different pathologies depending on the route of infection. These are cutaneous anthrax, typically identified by the appearance of a black eschar on the skin at the site of infection [2], gastrointestinal anthrax, which resembles generic food poisoning [3], and inhalational anthrax. Inhalational is the most serious form of anthrax infection and initially presents with a nonspecific prodrome resembling the flu followed by severe respiratory distress, septic shock, and death [4]. Unfortunately, other conditions present with similar symptoms, confounding an obvious diagnosis [3]. The ability of B. anthracis to form an environmentally hardened spore allows for aerosolized dispersion and has prompted its use as a bioterrorism agent [5] Inhalation of aerosolized spores results in a high percentage of morbidity and mortality due to the high exposure and infection potential. If diagnosis and proper medical intervention are not initiated early enough, the infection rapidly progresses to a point where antibiotic therapy is no longer effective due to the accumulation of lethal levels of toxin [6] and [7]. At this stage of the infection, the prognosis is poor; even with therapeutic intervention, inhalational anthrax has a mortality rate between 60 and 100% [5], [8] and [9].

Inhalational anthrax involves a complex series of host-pathogen interactions. The majority of the inhaled endospores are immediately ingested by pulmonary phagocytes and subsequently transported to the bloodstream through the lymphatic channels to the hilar and tracheobronchial lymph nodes [10], [11], [12] and [13]. During trafficking to these regional lymph nodes through the bloodstream, the endospores begin the germination process, resulting in the production of two exotoxins composed of binary combinations of protective antigen (PA)[1] and either lethal factor (LF) or edema factor (EF) [14]. These toxin proteins are analogous to other AB-type toxins and form lethal toxin (LT), from the combination of LF and PA, and/or edema toxin (ET), from the combination of EF and PA. Binding to PA occurs on the cell surface after cleavage and activation of full-length PA83 to PA63 by furin [14] and [15]. The activated PA63 conformer oligomerizes to form a heptamer that binds up to three molecules of LF, EF, or a mixture of the two [16] and [17]. The central role of PA during the intoxication process is further highlighted by its messenger RNA (mRNA) expression levels, which are reported to be 4-fold higher than LF and 14-fold higher than EF [18]. Following endocytosis of the toxin complex and subsequent acidification of the endosome, the PA63 heptamer inserts into the membrane, forming a channel through which LF and EF enter the cytosol [19]. Both toxins serve to disable the immune system. LF, a zinc-dependent endopeptidase, specifically cleaves mitogen-activated protein kinase kinases down-regulating both innate and acquired immune responses, whereas EF, an adenylate cyclase, incapacitates phagocytes and causes edema through cyclic AMP induction and accumulation of fluid [20]. The prominence of the PA fraction of the anthrax tripartite toxin and its elevated expression levels relative to the other toxin components during pathogenesis make it an ideal biomarker for diagnostic detection.

Traditional diagnosis of anthrax uses the patient's history and a battery of tests that evaluate standard morphological and phenotypic properties. These procedures involve culturing blood or cerebrospinal fluid overnight, followed by multiple hours of biochemical testing and microscopy [21]. Although definitive, the isolation of B. anthracis from biological samples is possible only late in the disease process [22]. Serological diagnosis is also an accepted technique that is sensitive and specific, but antibody responses to B. anthracis require between 8 and 12 days to develop [23]. Attempts to maintain sensitivity while reducing the time between sample collection and diagnosis have resulted in numerous genotypic identification methods using polymerase chain reaction (PCR) or reverse transcription (RT)-PCR amplification to detect anthrax-specific DNA or mRNA sequences, respectively [3]. Identification of B. anthracis infection has also been demonstrated with various immunoassays directed against key biomarkers that characterize anthrax, including spore coat antigens and toxins. These approaches are dependent on target acquisition and identification through the interaction of multiple antibodies and a chromogenic substrate [24], [25] and [26]. Unfortunately, the requirement of a chromogenic substrate limits both biomarker resolution and the detection limit (to ~1 ng/ml). For instance, sandwich enzyme-linked immunosorbent assays (ELISAs) developed for the detection of anthrax PA exotoxin using monoclonal and polyclonal antibodies achieve the same lower PA detection limit of approximately 1 ng/ml for a detection time of more than 4 to 5 h [25] and [27]. Development of fluorescence-based assays with increased sensitivity, such as immunoassay using europium nanoparticles (NPs) [26], fluorescent covalent microspheres [28], and fluorescence resonance energy transfer (FRET) assay [29], have protein sensitivity in a range from 10 pg/ml to 60 ng/ml and an assay PA detection time of more than 4 to 5 h. Recently reported approaches for anthrax protein toxins, such as assays based on multiwall carbon nanotube sensors [30] and on matrix-assisted laser desorption/ionization time-of-flight (MALDI-TOF) mass spectrometry [31], have relatively higher detection limits of 30 ng/ml and 5 pg/ml, respectively, whereas detection time, especially for the MALDI-TOF assay, is long and includes an overnight incubation stage. In essence, currently known anthrax toxin assays have a broad range of sensitivities and require multiple time-consuming incubations.

Direct detection of toxin in biological fluids following its production is an ideal approach to diagnosis because it avoids extended incubations associated with culturing and amplification. Recent advances in the field of fluorescence spectroscopy have yielded a new platform technology for fluorescence surface bioassays called microwave-accelerated metal-enhanced fluorescence (MAMEF). This technique reliably detects proteins [32], [33] and [34] and nucleic acids [35], [36] and [37] at nanogram levels and below from biological fluids within seconds. This ultra-fast technology is based on metal-enhanced fluorescence (MEF), a phenomenon that dramatically enhances chromophores' emission when in close proximity to silver NPs [38] and [39] and attached to the metal NPs. MEF is based on the specific coupling of both the ground and excited state fluorophores with the surface plasmon electrons of the proximal silver NPs, resulting in enhancement of emission and typically reducing the excited state lifetime [38] and [39]. Another component of the MAMEF technology is the use of low-power microwave irradiation of samples, which increases the rate of mass transportation and molecular diffusion, resulting in an increase in the analyte detection limit [40] and [41].

It would be advantageous to provide a detection assay system that has the ability to quickly identify non-toxic proteins in a sample before the combination of such non-toxic proteins to form a toxic protein and thereby providing early therapeutic intervention during the presymptomatic timeframe.

SUMMARY OF THE INVENTION

The present invention provides for a PA detection assay that is both rapid (<1 h) and ultra-sensitive (≈pg/ml) thereby providing for early diagnosis of the disease and its successful care.

The ultra-fast technique can be used for the detection of PA during presymptomatic *B. anthracis* infection, specifically identifying a protective antigen PA83 (such as Accession: P13423.2).

In one aspect, the present invention provides for a system for detecting a protective antigenic protein of a pathogenic microorganism in a sample suspected of including same, the system comprising:
  a. a substrate surface adapted for binding of the protective antigenic protein;
  b. metallic particles deposited on the substrate surface, wherein the metallic particles have a diameter from about 40 nm to about 120 nm and separated from each other with a distance from about 10 nm to 50 nm, and more preferably from about 10 nm to 30 nm;
  c. a first antibody having binding affinity for the protective antigen protein;
  d. a second antibody have binding affinity for the first antibody, wherein the second antibody comprises an at least one excitable molecule, wherein the excitable molecule is selected from the group of an intrinsic fluorophore, extrinsic fluorophore, fluorescent dye, and luminophores upon binding to the first antibody positions the excitable molecule from about 5 nm to about 200 nm from at least one adjacent metallic particles, preferably from about 5 nm to about 30 nm, and more preferably, 5 nm to about 20 nm;
  e. a source of electromagnetic energy to deliver radiation in a range of UV to IR and in an amount sufficient to excite the excitable molecule;
  f. a source of microwave energy in an amount sufficient to increase binding reactions in the system; and
  g. a detector to measure emissions from the excitable molecule.

The above system can be effectively used for determining the inclusion of the protective antigen PA83 of anthrax in a testing sample. Other target proteins may include proteins from a number of bacteria including *Vibrio cholerae, Bordetella pertussis, Bordetella bronchiseptica, staphylococci* (*S. aureus, S. epidermidis*), *streptococci* (*S. pneumoniae, S. pyogenes, S. agalactiae*), *Helicobacter pylori, Escherichia coli* (Enterotoxigenic *E. coli*, Enteroaggregative *E. coli*), *Shigella flexneri, Chlamydia pneumoniae, Enterococcus faecalis, Klebsiella pneumoniae, Haemophilus influenzae, Moraxella catarrhalis, Borellia afzelii, Campylobacter jejuni, Neisseria meningitides*, etc.

The substrate surface may be fabricated of glass, quartz, plastics (such as on the bottom of HTS plates, polystyrene, polycarbonate), semiconductors, paper, cellulose, cotton, nylon, silk, sapphire, diamond, ruby, dielectric materials, combinations thereof or any material that provides sufficient stability for placement of the metallic particles and also adapted for binding of the protective antigenic protein. The metallic particles are preferably fabricated from Silver, Gold, Copper, Aluminum, Zinc, Nickel, Palladium, Tungsten, Platinum, Germanium, Indium, Iron, Tin, Rhodium or combinations thereof.

In another aspect, the present invention provides for a method for detecting a target protein, such as a protective antigen, in a testing sample, the method comprising:
  a. providing a system comprising:
    i) a substrate surface comprising immobilized metallic particles wherein the substrate surface is adapted for binding of the target protein;
    ii) metallic particles deposited on the substrate surface, wherein the metallic particles have a diameter from about 40 nm to about 120 nm and separated from each other with a distance from about 10 nm to 50 nm, and more preferably from about 10 nm to 30 nm;
  b. introducing the testing sample to the substrate surface for a sufficient time and under conditions wherein any target protein in the testing sample binds to the substrate surface and positioned between the metallic particles and not on the metallic particles;
  c. introducing a first antibody having affinity for the target protein under conditions sufficient for the binding of the first antibody to form a target protein/first antibody complex while applying microwave energy in an amount sufficient to increase the binding of the first antibody to the target protein;
  d. introducing a second antibody having affinity for the first antibody, wherein the second antibody comprises at least one excitable molecule, wherein the excitable molecule is selected from the group of an intrinsic fluorophore, extrinsic fluorophore, fluorescent dye, and luminophores and wherein binding to the first antibody positions the excitable molecule from about 5 nm to about 200 nm from at least one adjacent metallic particles, preferably from about 5 nm to about 30 nm, and more preferably, 5 nm to about 20 nm;

e. applying electromagnetic energy in an amount sufficient to excite the excitable molecule; and
f. measuring the emissions from the system to determine the existence of any target protein.

In a still further aspect, the present invention relates to an assay using High Throughput Screening (HTS) for testing of a target protein in a testing sample, the method comprising:
a) providing a well plate used in HTS systems comprising a multiplicity of wells wherein the surface of the wells is adapted for binding of the target protein;
b) introducing metallic particles into the wells, wherein the metallic particles are deposited on the substrate surface, wherein the metallic particles have a diameter from about 40 nm to about 120 nm and separated from each other with a distance from about 10 nm to 50 nm, and more preferably from about 10 nm to 30 nm;
c) introducing the testing sample suspected of including the target protein for binding to the surface of the well and positioned on the surface and between the metallic particles and not binding to the metallic particles;
d) introducing a first antibody having affinity for the target protein under conditions sufficient for the binding of the first antibody to form a target protein/first antibody complex while applying microwave energy in an amount sufficient to increase the binding of the first antibody to the target protein;
e) introducing a second antibody having affinity for the first antibody, wherein the second antibody comprises at least one excitable molecule, wherein the excitable molecule is selected from the group of an intrinsic fluorophore, extrinsic fluorophore, fluorescent dye, and luminophores and wherein binding to the first antibody positions the excitable molecule from about 5 nm to about 200 nm from at least one adjacent metallic particles, preferably from about 5 nm to about 30 nm, and more preferably, 5 nm to about 20 nm;
f) applying electromagnetic energy in an amount sufficient to excite the excitable molecule; and
g) measuring the emissions from the system to determine the existence of any target protein.

Other aspects and advantages of the invention will be more fully apparent from the ensuing disclosure and appended claims.

DETAILED DESCRIPTION OF THE INVENTION

Figure 1:
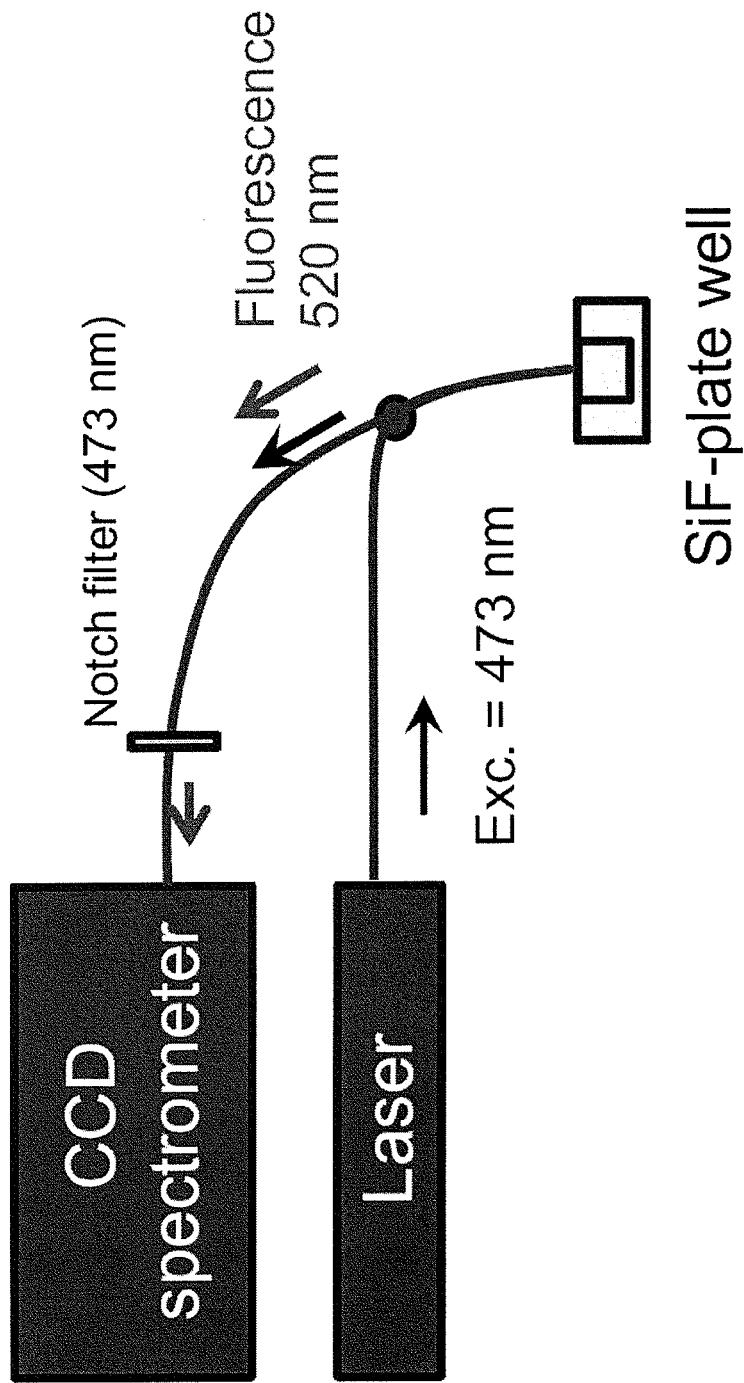
FIG. 1 shows the experimental setup for the MEF-PA assay. A bitruncated fiber was used both to deliver the excitation light to the sample and to collect the fluorescence, which after passing through a Notch filter to remove the 473-nm laser light falls incident on a CCD spectrometer.

The present invention provides for a novel MAMEF-PA assay that was designed especially for the detection of low levels of non-toxic exotoxin, such as the protective antigen (PA) of anthrax in biological fluids. The present assay uses a combination of the metal-enhanced fluorescence MEF effect and microwave-accelerated PA protein surface absorption. Technologically, the proposed MEF-PA assay uses standard 96-well plastic plates modified with silver island films (SiFs) grown within the wells. Microwave irradiation rapidly accelerates PA deposition onto the surface ("rapid catch"), significantly speeding up the MEF-PA assay and resulting in a total assay run time of less than 40 min with an analytical sensitivity of less than 1 pg/ml PA.

It must be noted that, as used in this specification and the appended claims, the singular forms "a," "an," and "the" include plural references unless the content clearly dictates otherwise.

The term "protective antigen" can include non-toxic proteins that must be combined with other proteins to lead to a toxin, such as found in *Bacillus anthracis*. The present invention may also be used to for the detection of proteins as described by Xiang in [46] and [47].

"Fluorophore," and "fluorescence label," used interchangeably herein, means any substance that emits electromagnetic energy such as light at a certain wavelength (emission wavelength) when the substance is illuminated by radiation of a different wavelength (excitation wavelength) and is intended to encompass a chemical or biochemical molecule or fragments thereof that is capable of interacting or reacting specifically with an analyte of interest in a sample to provide one or more optical signals. Additionally fluorophore includes both extrinsic and intrinsic fluorophores. Extrinsic fluorophore refer to fluorophores bound to another substance. Intrinsic fluorophores refer to substances that are fluorophores themselves. Exemplary fluorophores include but are not limited to those listed in the Molecular Probes Catalogue which is incorporated by reference herein.

Representative fluorophores include but are not limited to Alexa Fluor® 350, Dansyl Chloride (DNS-Cl), 5-(iodoacetamida)fluoroscein (5-IAF); fluoroscein 5-isothiocyanate (FITC), tetramethylrhodamine 5-(and 6-)isothiocyanate (TRITC), 6-acryloyl-2-dimethylaminonaphthalene (acrylodan), 7-nitrobenzo-2-oxa-1,3,-diazol-4-yl chloride (NBD-Cl), ethidium bromide, Lucifer Yellow, 5-carboxyrhodamine 6G hydrochloride, Lissamine rhodamine B sulfonyl chloride, Texas Red™. sulfonyl chloride, BODIPY™, naphthalamine sulfonic acids including but not limited to 1-anilinonaphthalene-8-sulfonic acid (ANS) and 6-(p-toluidinyl) naphthalen-e-2-sulfonic acid (TNS), Anthroyl fatty acid, DPH, Parinaric acid, TMA-DPH, Fluorenyl fatty acid, Fluorescein-phosphatidylethanolamine, Texas red-phosphatidylethanolamine, Pyrenyl-phophatidylcholine, Fluorenyl-phosphotidylcholine, Merocyanine 540, 1-(3-sulfonatopropyl)-4-[-.beta.-[2 [(di-n-butylamino)-6-naphthyl]vinyl]pyridinium betaine (Naphtyl Styryl), 3,3'dipropylthiadicarbocyanine (diS-$C_3$-(5)), 4-(p-dipentyl aminostyryl)-1-methylpyridinium (di-5-ASP), Cy-3 Iodo Acetamide, Cy-5-N-Hydroxysuccinimide, Cy-7-Isothiocyanate, rhodamine 800, IR-125, Thiazole Orange, Azure B, Nile Blue, Al Phthalocyanine, Oxaxine 1,4',6-diamidino-2-phenylindole (DAPI), Hoechst 33342, TOTO, Acridine Orange, Ethidium Homodimer, N(ethoxycarbonylmethyl)-6-methoxyquinolinium (MQAE), Fura-2, Calcium Green, Carboxy SNARF-6, BAPTA, coumarin, phytofluors, Coronene, and metal-ligand complexes.

Representative intrinsic fluorophores include but are not limited to organic compounds having aromatic ring structures including but not limited to NADH, FAD, tyrosine, tryptophan, purines, pyrimidines, lipids, fatty acids, nucleic acids, nucleotides, nucleosides, amino acids, proteins, peptides, DNA, RNA, sugars, and vitamins. Additional suitable fluorophores include enzyme-cofactors; lanthanide, green fluorescent protein, yellow fluorescent protein, red fluorescent protein, or mutants and derivatives thereof.

Fluorophores with high radiative rates have high quantum yields and short lifetimes. Increasing the quantum yield requires decreasing the non-radiative rates $k_{nr}$, which is often only accomplished when using a low solution temperature or a fluorophore bound in a more rigid environment. The natural lifetime of a fluorophore, $\tau_n$, is the inverse of the radiative decay rate or the lifetime which would be observed if their quantum yields were unity. This value is determined by the oscillator strength (extinction coefficient) of the electronic transition. Hence, for almost all examples currently employed in fluorescence spectroscopy, the radiative decay rate is essentially constant. The modification and control of the radiative rate have also been referred as Radiative Decay Engineering (RDE), or "lightening rod" fluorescence enhancement effect. For example, enhanced intrinsic DNA fluorescence above metallic particles has recently been observed, which is typically not readily observable because of DNA's very low quantum yield of less than $10^{-4}$. The second favorable "lightening rod" effect also increases the fluorescence intensity by locally enhanced excitation. In this case, emission of fluorophores can be substantially enhanced irrespective of their quantum yields.

The reduction in lifetime of a fluorophore near a metal is due to an interaction between the fluorophore and metal particle, which enhances the radiative decay rate (quantum yield increase) or depending on distance, $d^{-3}$, causes quenching. It should be noted that lifetimes of fluorophores with high quantum yields (0.5) would decrease substantially more than the lifetimes of those with low quantum yields (0.1 and 0.01). A shorter excited-state lifetime also allows less photochemical reactions, which subsequently results in an increased fluorophore photostability. Notably, the use of low quantum yield fluorophores would lead to much larger fluorescence enhancements (i.e. $1/Q_0$) and could significantly reduce unwanted background emission from fluorophores distal from the silvered assay.

Fluorophore photostability is a primary concern in many applications of fluorescence. This is particularly true in single molecule spectroscopy. A shorter lifetime also allows for a larger photon flux. The maximum number of photons that are emitted each second by a fluorophore is roughly limited by the lifetime of its excited state. For example, a 10 ns lifetime can yield about $10^8$ photons per second per molecule, but in practice, only $10^3$ photons can be readily observed. The small number of observed photons is typically due to both photo-destruction and isotropic emission. If a metal surface decreases the lifetime, one can obtain more photons per second per molecule by appropriately increasing the incident intensity.

On the other hand, the metal-enhanced fluorescence provides enhanced intensity, while simultaneously shortening the lifetime. That is, it may be possible to decrease the excitation intensity, yet still see a significant increase in the emission intensity and photostability.

The emission enhancement may be observed at distances according to the type of fluorophore to be detected and the type, shape of the metal material, noting a difference between a film and a metallic island or colloid. For example, emission enhancement may be observed when a fluorophore is positioned from about 5 nm to about 200 nm from the metal surfaces. Preferable distances are about 5 nm to about 40 nm, and more preferably, 5 nm to about 20 nm to metal surfaces. At this scale, there are few phenomena that provide opportunities for new levels of sensing, manipulation, and control. In addition, devices at this scale may lead to dramatically enhanced performance, sensitivity, and reliability with dramatically decreased size, weight, and therefore cost.

Attaching of the fluorophore to a probe may be achieved by any of the techniques familiar to those skilled in the art. For example, the fluorophore may be covalently attached to the bimolecular probe by methods disclosed in U.S. Pat. No. 5,194,300 (Cheung) and U.S. Pat. No. 4,774,189 (Schwartz).

Any chemiluminescent species may be used in the present invention that provides for a chemical reaction which produces a detectable reaction (observed emission) wherein the excited state responsible for the observed emission including, but not limited to the following excitation mechanisms:

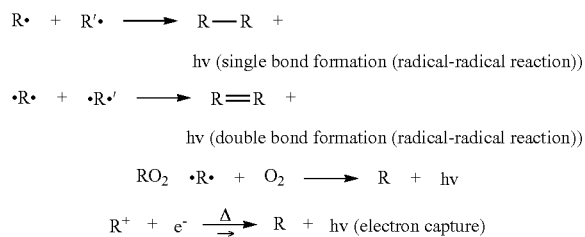

Examples of suitable chemiluminescence detector molecules include but without limitation, peroxidase, bacterial luciferase, firefly luciferase, functionalized iron-porphyrin derivatives, luminal, isoluminol, acridinium esters, sulfonamide and others. A recent chemiluminescent label includes xanthine oxidase with hypoxanthine as substrate. The triggering agent contains perborate, a Fe-EDTA complex and luminol. Choice of the particular chemiluminescence labels depends upon several factors which include the cost of preparing labeled members, the method to be used for covalent coupling to the detector molecule, and the size of the detector molecules and/or chemiluminescence label. Correspondingly, the choice of chemiluminescence triggering agent will depend upon the particular chemiluminescence label being used.

Chemiluminescent reactions have been intensely studied and are well documented in the literature. For example, peroxidase is well suited for attachment to the detector molecule for use as a chemiluminescence. The triggering agent effective for inducing light emission in the first reaction would then comprise hydrogen peroxide and luminol. Other triggering agents which could also be used to induce a light response in the presence of peroxidase include isobutyraldehyde and oxygen. Procedures for labeling detector molecules, such as antibodies or antigens with peroxidase are known in the art. For example, to prepare peroxidase-labeled antibodies or antigens, peroxidase and antigens or antibodies are each reacted with N-succinimidyl 3-(2-pyridyldithio) propionate (hereinafter SPDP) separately. SPDP-labeled peroxidase, or SPDP-labeled antigen or antibody is then reacted with dithiothreitol to produce thiol-labeled peroxidase, or thiol-labeled antigen or antibody. The thiol derivative is then allowed to couple with the SPDP-labeled antigen or antibody, or SPDP-labeled peroxidase.

The present invention further comprises a detection device for detecting emissions including, but not limited to visual inspection, digital (CCD) cameras, video cameras, photographic film, or the use of current instrumentation such as laser scanning devices, fluorometers, luminometers, photodiodes, quantum counters, plate readers, epifluorescence microscopes, fluorescence correlation spectroscopy, scanning microscopes, confocal microscopes, capillary electrophoresis detectors, or other light detector capable of detecting the presence, location, intensity, excitation and emission spectra, fluorescence polarization, fluorescence lifetime, and other physical properties of the fluorescent signal.

Excitation light sources can include arc lamps and lasers, natural sunlight, laser diodes and light emitting diode source, and both single and multiple photon excitation sources. In another embodiment, use of a Ti-sapphire laser, Laser Diode (LD) or Light Emitting Diode Sources (LEDs) may be used with the RNA assay of the present invention. For example, using 2-photon excitation at 700-1000 nm and also using short pulse width (<50 pi), high repetition rate (1-80 MHz), laser diode and LED (1 ns, 1-10 MHz) sources.

The enhanced sensitivity of the assay using 2-photon excitation, as compared to 1-photon, can be shown by using series dilution with RNA, initially with the Ti-Sapphire system, and later with LEDs and LDs. If a fluorophore absorbs two photons simultaneously, it will absorb enough energy to be raised to an excited state. The fluorophore will then emit a single photon with a wavelength that depends on the fluorophore used and typically in the visible spectra. The use of the Ti-sapphire laser with infrared light has an added benefit, that being, longer wavelengths are scattered less, which is beneficial for high-resolution imaging. Importantly, there is reduced background signal level gained by using 2-photon excitation as compared to 1-photon excitation by utilizing localized excitation nearby metallic nanoparticles.

In another embodiment, the application of low level microwave heating of the sample may be used to speed up any chemical/biochemical kinetics within the system. Notably, low level microwaves do not destroy or denature proteins, DNA, or RNA, but instead heat the sample sufficiently to provide for accelerated kinetics such as binding or hybridization. In addition, the microwaves are not scattered by the metallic nanoparticles, which is contrary to most metal objects, such as that recognized by placing a spoon in a microwave oven.

Microwaves (about 0.3 to about 300 GHz) lie between the infrared and radiofrequency electromagnetic radiations. It is widely thought that microwaves accelerate chemical and biochemical reactions by the heating effect, where the heating essentially follows the principle of microwave dielectric loss. Polar molecules absorb microwave radiation through dipole rotations and hence are heated, where as non-polar molecules do not absorb due to lower dielectric constants are thus not heated. The polar molecules align themselves with the external applied field. In the conventional microwave oven cavity employed in this work, the radiation frequency (2450 MHz) changes sign $2.45 \times 10^9$ times per second. Heating occurs due to the torsional effect as the polar molecules rotate back and forth, continually realigning with the changing field, the molecular rotations being slower than the changing electric field. The dielectric constant, the ability of a molecule to be polarized by an electric field, indicates the capacity of the medium to be microwave heated. Thus, solvents such as water, methanol and dimethyl formamide are easily heated, whereas microwaves are effectively transparent to hexane, toluene and diethylether. For metals, the attenuation of microwave radiation arises from the creation of currents resulting from charge carriers being displaced by the electric field. These conductance electrons are extremely mobile and unlike water molecules can be completely polarized in 10-18 s. In microwave cavity used in the present invention, the time required for the applied electric field to be reversed is far longer than this, in fact many orders of magnitude. If the metal particles are large, or form continuous strips, then large potential differences can result, which can produce dramatic discharges if they are large enough to break down the electric resistance of the medium separating the large metal particles. Interestingly, and most appropriate for the new assay platform described herein, small metal particles do not generate sufficiently large potential differences for this "arcing" phenomenon to occur. However, the charge carriers which are displaced by the electric field are subject to resistance in the medium in which they travel due to collisions with the lattice phonons. This leads to Ohmic heating of the metallic structures in addition to the heating of any surface polar molecules. Intuitively, this leads to localized heating around the metallic structures in addition to the solvent, rapidly accelerating assay kinetics.

In the present invention, microwave radiation may be provided by an electromagnetic source having a frequency in a range between 0.3 and 10 GHz, more preferably from about 1 GHz to about 3 GHz and a power level in a range between about 10 mwatts and 700 watts, more preferably from 100 watts to about 700 watts. Any source, known to one skilled in the art may be used, such as a laser that emits light, wherein light is used in its broad sense, meaning electromagnetic radiation which propagates through space and includes not only visible light, but also infrared, ultraviolet and microwave radiation. Thus, a single instrument placed above the surface of the assay can be used to generate the microwave energy and energy to excite fluorescing molecules. The light can be emitted from a fiber continuously or intermittently, as desired, to maintain the metallic particles at a predetermined temperature such that it is capable of increasing the speed of chemical reactions within the assay system. The microwave radiation may be emitted continuously or intermittently (pulsed), as desired. In the alternative, microwave energy can be supplied through a hollow wave guide for conveying microwave energy from a suitable magnetron. The microwave energy is preferably adjusted to cause an increase of heat within the metallic material without causing damage to any biological materials in the assay system.

Although fluorescence, chemiluminescence and/or bioluminescence detection has been successfully implemented, the sensitivity and specificity of these reactions require further improvements to facilitate early diagnosis of the prevalence of disease. In addition, most protein detection methodologies, most notably western blotting, are still not reliable methods for accurate quantification of low protein concentrations without investing in high-sensitivity detection schemes. Protein detection methodologies are also limited by antigen-antibody recognition steps that are generally kinetically very slow and require long incubation times; e.g., western blots require processing times in excess of 4 h. Thus, both the rapidity and sensitivity of small-molecule assays are still critical issues to be addressed to improve assay detection. As such the use of low intensity ultrasound will increase the rapidity of the assay.

There are many important assays that can directly benefit from enhanced signal intensities and quicker kinetics. For example, myoglobin concentrations for heart attack patients, patients of toxic shock and pancreatitis. All of these assays are widely used in hospitals emergency rooms with assay times of greater than 30 minutes. Thus, the present invention can be used for points-of-care clinical assessment in emergency rooms.

Thus it would be advantageous to increase speed of any chemical or biochemical reaction by using any device capable of generating and transmitting acoustic energy through any medium to transit ultrasonic atomizing energy. The ultrasonic emitting device can be placed in either the interior of a vessel used in a detection system or positioned adjacent thereto for transmitting energy into the vessel. The device may include components for the traditional electromagnetic stimulation of piezoelectric transducers, (man-made or naturally occurring), purely mechanical devices (such as high frequency air whistles or microphones), and laser devices. Individual components for acoustic energy systems are commercially available from a wide variety of manufacturers, which can be configured to particular applications and frequency ranges. (See Thomas Directory of American Manufacturers, Photonics Buyer's Guide, 1996, Microwave and RF, and Electronic Engineer's Master Catalogue).

Any oscillator or signal generator that produces a signal with predetermined characteristics such as frequency, mode, pulse duration, shape, and repetition rate may be used to generate acoustic frequencies for applying to the system of the present invention. Various oscillators or signal generators can be commercially purchased from a wide variety of manufacturers and in a variety of designs configured to particular applications and frequencies. Applicable transducers will include types that produce an acoustic wave within a range of frequencies (broadband) or for one specific frequency (narrowband) for frequencies ranging from hertz to gigahertz.

The acoustic delivery system will be variable depending on the application. For example, acoustic energy waves can be transmitted into liquid or solid source material either by direct contact of the source material with a transducer, or by coupling of transmission of the acoustic wave through another medium, which is itself in direct contact with the source material. If the source material is a liquid, a transducer can be placed in the liquid source material, or the walls of the vaporization vessel can be fabricated of a material that acts as a transducer thereby placing the liquid source material in direct contact with the transducer. Additionally, an acoustic energy emitting device may be positioned on the exterior of a system container for transmitting the appropriate energy. If the source material is a solid, a transducer can be placed in direct contact with it or the solid source material can be placed in a gas or liquid that is used as a coupling agent.

In the preferred acoustic frequencies any system that generates acoustic energy may be utilized. Preferably, the output of the ultrasonic generator is of a sufficient frequency to provide a movement flow within the system vessel to move molecules to the source of binding or reaction site without causing a large increase of heat in the system. For example, using the power output of 0.5 to 50 W at a frequency of 10 to 200 kHz, and more preferably from about 20 to 60 kHz and most preferably at about 40 kHz.

To obtain the maximum transfer of acoustical energy from one medium to another, the characteristic acoustical impedance of each medium is preferably as nearly equal to the other as possible. The matching medium is sandwiched between the other two and should be the appropriate thickness relative to the wavelength of the sound transmitted, and its acoustical impedance R should be nearly equal to ($R_1$:$R_2$). Any impedance matching device that is commercially available can be utilized in the present invention.

The system may include ultrasonic vessels wherein at least a section of the vessel includes a transducer such as a piezoelectric transducer to generate acoustic vibrations. Such transducers can be located in the bottom of a vessel or in a plate whereon a vessel may be placed. Further such transducers can be placed at different levels on the vessel walls to enhance fluid flow within the vessel.

The present invention provides enhanced emissions using metallized particles of elliptical, spherical, triangular or rod-like forms. In exemplary cases, the elliptical particles have aspect ratios of 3/2, and the spherical particles have diameters of 20-60 nm. However, the invention is not limited to any particular geometry. Using known coating techniques, the placement of metallic islands could be controlled precisely, as close as from about 10 nm to about 50 nm apart.

In one embodiment the metallic particle may be prepared by reduction of metal ions using various reducing agents, using technique known to one skilled in the art. For example, sodium hydroxide may be added to a rapidly stirred silver nitrate solution forming a brown precipitate. Then ammonium hydroxide is added to re-dissolve the precipitate. The solution is cooled and dried quartz slides are added to the beaker, followed by glucose. After stirring for 2 minutes, the mixture is warmed to 30° C. After 10-15 minutes, the mixture turns yellow-green and becomes cloudy. A thin film of silver particles has formed on the slides as can be seen from their brown green color. The slides are rinsed with pure water prior to use.

Particles can be prepared as suspensions by citrate reduction metals. Preferred metals are silver and gold. Again, gold may be used because of the absorption of gold at shorter wavelengths. The size of the colloids and their homogeneity can be determined by the extensive publications on the optical properties of metal particles available and the effects of interface chemistry on the optical property of particles.

Silver island films can be formed by a chemical reduction of a silver salt on the quartz surface, which are relatively simple to fabricate.

Metal particles can be bound to a surface by placing functional chemical groups such as cyanide (CN), amine ($NH_2$) or thiol (SH), on a glass or polymer substrate. Metal colloids are known to spontaneously bind to such surfaces with high affinity. Positioning of the biomolecule or metal particle at a desired distance can be achieved by using a film. The film may be a polymer film, a Langmuir-Blodgett film or an oxide film.

Substrate surfaces adapted for binding of proteins may include a number of commercially available assay surfaces and trays, including surfaces such as nitrocellulose surfaces, polyvinylidene fluoride, polystyrene, polypropylene, etc. In the alternative, plates can be prepared by coating of a resin on the surface of the plates that binds with proteins including, nitrocellulose surfaces, polyvinylidene fluoride, polystyrene, and or polypropylene and then the metallic particles can be deposited on the surface. Further the resin can be applied to the surface in a patterned method so that the subsequently deposited metallic particles are not deposited on the resin but instead directly on an untreated surface.

Examples

Materials and Methods

Silver nitrate (99.9%), sodium hydroxide (99.996%), ammonium hydroxide (30%), and d-glucose were purchased from Sigma-Aldrich (USA). Immulon 4 HBX 1×12 Strip flat-bottom plates were purchased from Thermo Scientific (USA).

Recombinant full-length PA (PA83) protein (Accession: ACF33508.1 or AAR88321.1) primary antibody for PA (IQNPA anti-PA), was supplied by IQ Corporation (Netherlands) and has been described previously [42]. Secondary antibody, fluorescein isothiocyanate (FITC) Pierce Rabbit Anti-Human Immunoglobulin G (IgG, FC fragment specific, fluorescein conjugated), was purchased from Thermo Scientific. Milk Diluent/Blocking solution was purchased from KPL (USA). SuperBlock blocking buffer in phosphate-buffered saline (PBS) was obtained from Thermo Scientific.

Preparation of SiFs

Preparation of silver island films (SiFs) on the bottom of Immulon 4 HBX plate wells was undertaken using a modified protocol as described previously [40]. This includes the preparation of a silvering solution. Here 200 µl of sodium hydroxide solution (0.5%, w/v) is added to 60 ml of AgNO3 (0.83%, w/v) and the solution becomes brown and cloudy, after which 2 ml of ammonium hydroxide (30% solution) is added until the solution becomes clear. The solution is then cooled down on ice to 10° C., and 15 ml of fresh d-glucose solution (4.8%, w/v) is added while stirring. The silvering solution is then loaded into preheated (40° C.) plate wells for 2 min, followed by cooling on ice for 4 min. The plate is then placed on a heater (40° C.) for different deposition times (DTs) from 2 to 12 min. The plate is then washed several times with deionized water and dried with a stream of nitrogen gas. The optical density (OD) spectra (absorption spectra) of SiF plates were measured using a Cary 50 Bio UV-VIS (ultraviolet-visible) Spectrophotometer equipped with a 50 MPR Microplate Reader (Varian).

Measurements of Fluorescence

Fluorescence measurements of the fluorescein-labeled antibody in plate wells as well as excitation of emission were made by using a coupled fiber system, as shown in FIG. 1, attached to a Fiber Optic CCD (charge-coupled device) Spectrometer (HD2000) from Ocean Optics (USA). Excitation was undertaken using a 473-nm CW laser line. Notch and LongPass RazorEdge filters (Semrock, USA) were used to cut off the excitation light in the detection channel and to maximize the detection signal.

Attachment of PA to Silver-Coated Immulon 4 HBX Plates

PA at different concentrations was dissolved in 1:20 (v/v) diluted milk diluent/blocking solution. Attachment of the PA protein to SiF plate wells was performed by incubation of PA solution (80 µl/well) at ambient temperature for 30 min or by microwave irradiation for different times (5-30 s) in a microwave cavity using a GE Compact Microwave (model JES735BF, frequency=2.45 GHz, power=700 W). The microwave irradiation power was reduced to 20%, which corresponded to 140 W over the entire cavity. After incubation (microwave irradiation), plate wells were washed extensively with deionized water and filled with buffer.

Formation of Antibodies/PA Complex

Notably two protocols were used for the antibody attachment to PA.

Protocol 1

Protocol 1 is a commonly used procedure for standard ELISAs and approaches. It includes the following steps: add the PA sample into plate wells and incubating for 60 min; wash the wells to remove unattached protein; block the unoccupied surface with bovine serum albumin (BSA); add the primary antibody (1), [anti-PA]=50 nM, and incubate for 15 \ min; the 1 binds to PA; wash to remove unattached 1; add secondary antibody (2), [mouse anti-human IgG-biotin] =50 nM, and incubate for 15 min; the 2 antibody attaches to 1; wash to remove unattached 2; add streptaviding FITC (St-F), [St-F]=50 nM, and incubate for 15 min; the St-F binds to biotin-2 complex; wash to remove unattached streptavidin; fill wells with buffer.

Protocol 2

Protocol 2 is a modification of the first protocol and was designed specifically to be much more rapid by reducing the total number of steps (reagents) used for antibody binding and "visualization" of PA on the surface. After incubating PA/milk (Milk Diluent/Blocking solution) in the wells as in protocol 1, the surface was rapidly blocked with SuperBlock solution without incubation; that is, after loading SuperBlock solution into wells, it was immediately removed and the wells were refilled. The procedure was repeated three times. Instead of using the streptaviding biotin system in this protocol, a fluorescein-labeled secondary antibody was used. This omission removes one incubation/washing step, thereby speeding up the process. Binding of antibodies to the PA on the plate wells' surface was performed by adding 80 µl of the milk solution containing a 1:1 (mol/mol) preformed complex of the primary and secondary antibodies (concentration of antibodies=50 nM). Plates were incubated at ambient temperature for 30 min.

FDTD Numerical Simulations

The two-dimensional finite difference time domain (FDTD) simulations were used to simulate the effect of nanoparticle (NP) density, which increases during wet deposition of silver on glass slides, with the favorable effect of increasing the electric field intensity between the NPs. For the simulations, the incident far field was defined as a plane wave with a wave vector that is normal to the injection surface, and the scattered and total fields were monitored during the simulation such that the total or scattered transmission could be measured. The excitation light (473 nm) was incident on the 200-nm silver NPs from the bottom along the y axis. Two NPs were attached to the glass slide. The distance between two silver NPs was systematically changed from 70 to 10 nm. Using FDTD Solutions software (Lumerical, Canada), the simulation region was set to 600× 600 nm$^2$ with high mesh accuracy. To minimize simulation times and maximize the resolution of visualizing field enhancement around the metal particles, a mesh override region was set to 0.1 nm. The overall simulation time was set to 100 fs.

Results and Discussion

Physical Characterization of SiF Plates

Figure 2:
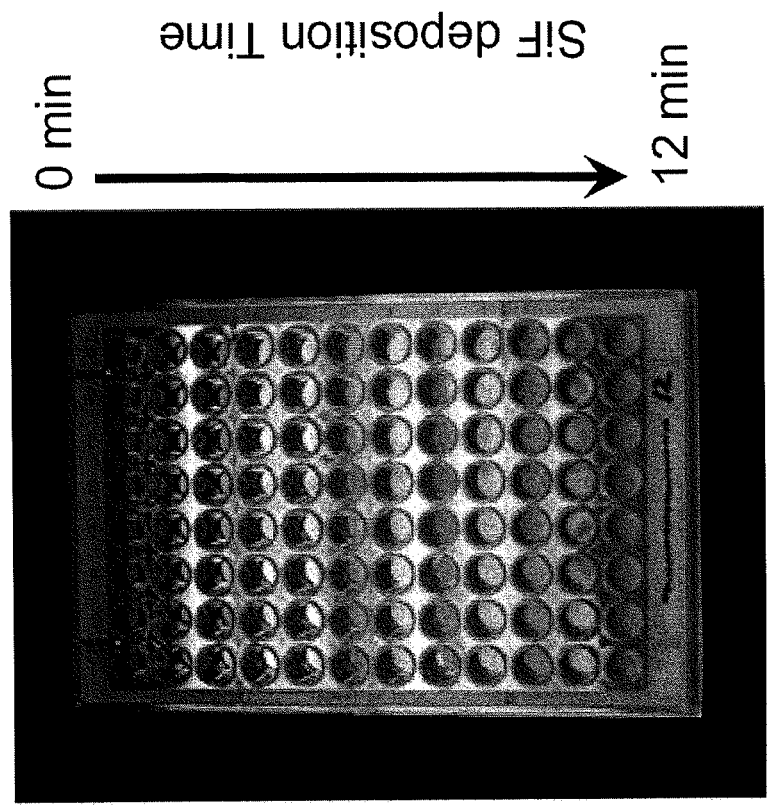
FIG. 2 shows photographs of the original Immulon 4 HBX plate (left) and a silvered plate (SiF plate) (right). The silver DT was varied from 0 to 12 min (from the plate top to bottom).
Figure 2:
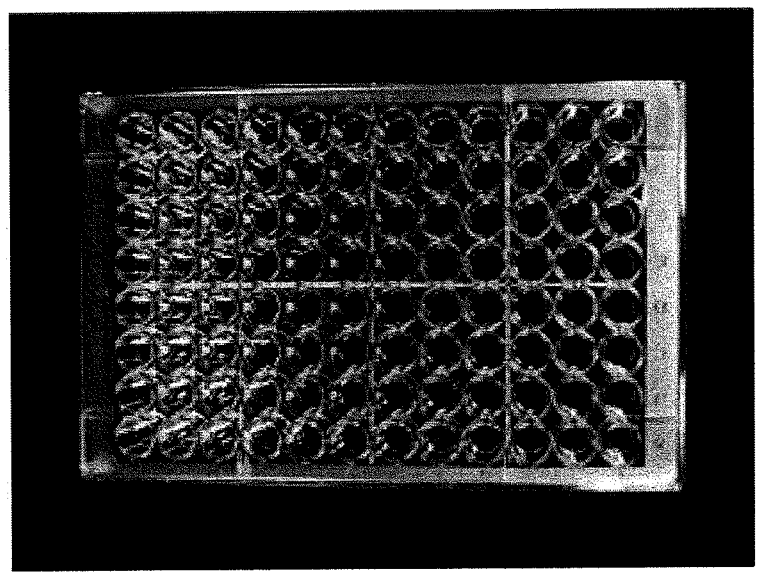
Figure 3:
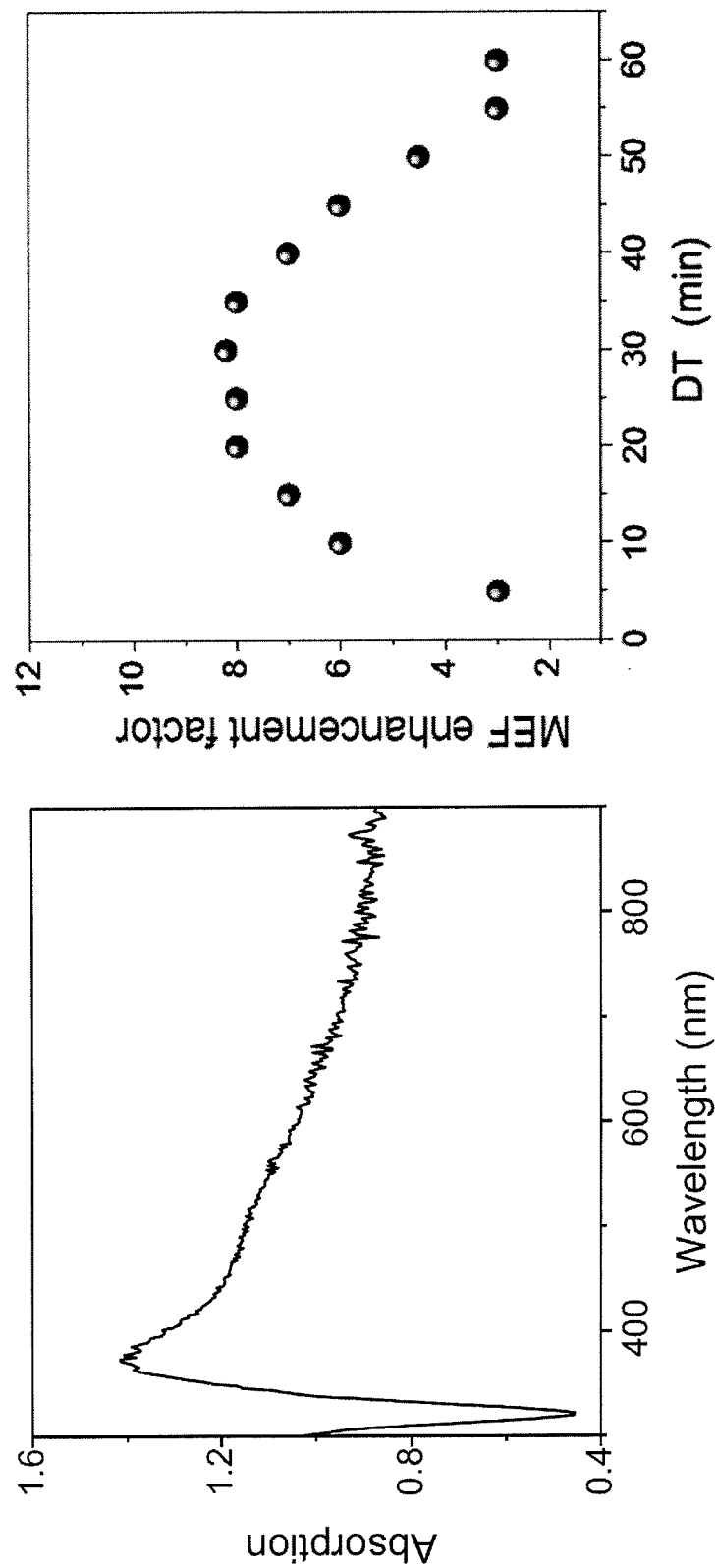
FIG. 3 shows (Left): Plasmon resonance absorption band of silver NPs deposited into HBX plate wells (DT=15 min). (Right): Dependence of fluorescein emission on SiF DT. Excitation was at 473 nm using a CW laser line.

FIG. 2 shows photographs of the original and silver-modified Immulon 4 HBX plates. The silver DT within wells was progressively increased from 0 to 12 min by row but remains constant along the columns to help understand the role of NP density on enhanced fluorescence. The change in silver DT changes the silver NPs' size and density and subsequently their physical properties on MEF. In particular, it changes the spectral position of the plasmon resonance band, which is a result of the specific change in the absorption and scattering components of plasmon electrons, coupling with the far-field incident light [43]. FIG. 3 shows a characteristic plasmon resonance absorption spectrum of SiFs deposited within Immulon 4 HBX plate wells. The magnitude of the plasmon scattering portion of the extinction spectra increases with the NPs' size and density and shifts to the red [38] and [43]. FIG. 2 (right panel) clearly demonstrates this physical effect; an increase in silver DT changes the color of the SiFs' reflection from gold-yellow (low DT) to red-gray (greater DT). The color of the SiFs along each row is identical and corresponds to the constant silver DT.

The MEF-enhancing property of the SiF wells was further characterized by using standard solutions of fluorescein [43] and [44]. FIG. 3 (right panel) shows the dependence of the MEF effect (i.e., the ratio of fluorescence intensity measured in the SiF plate well as compared with the intensity of the dye from the original nonsilvered [control] wells). The dependence is nonlinear. The observed MEF effect increases from the onset of deposition, reaching a maximum MEF value of approximately 8 for DT>10 min. A further increase in DT leads to a decline in the MEF enhancement factor. The decrease in the MEF effect at DT>35 min is attributed to the formation of a continuous metal film on the well bottom and the subsequent disappearance of NPs, which are critical for the MEF effect [43].

For assay development, DTs optimized for the maximum MEF effect were used to subsequently maximize the fluorescence enhancement of the fluorescein-labeled antibody. Origin of MEF enhancement of the PA-antibody dye emission and the MEF effect optimization for Immulon 4 HBX SiF plates. The PA protein effectively binds to the high protein capacity hydrophilic resin that covers the surface of the Immulon 4 HBX plate well bottom. This property of PA can be readily used for its detection using standard ELISA approaches, using horseradish peroxidase (HRP)-based chemiluminescence approaches [45], or in the present invention using a fluorescein-labeled biotin-streptavidin system (i.e., using a fluorescence signal).

Figure 4:
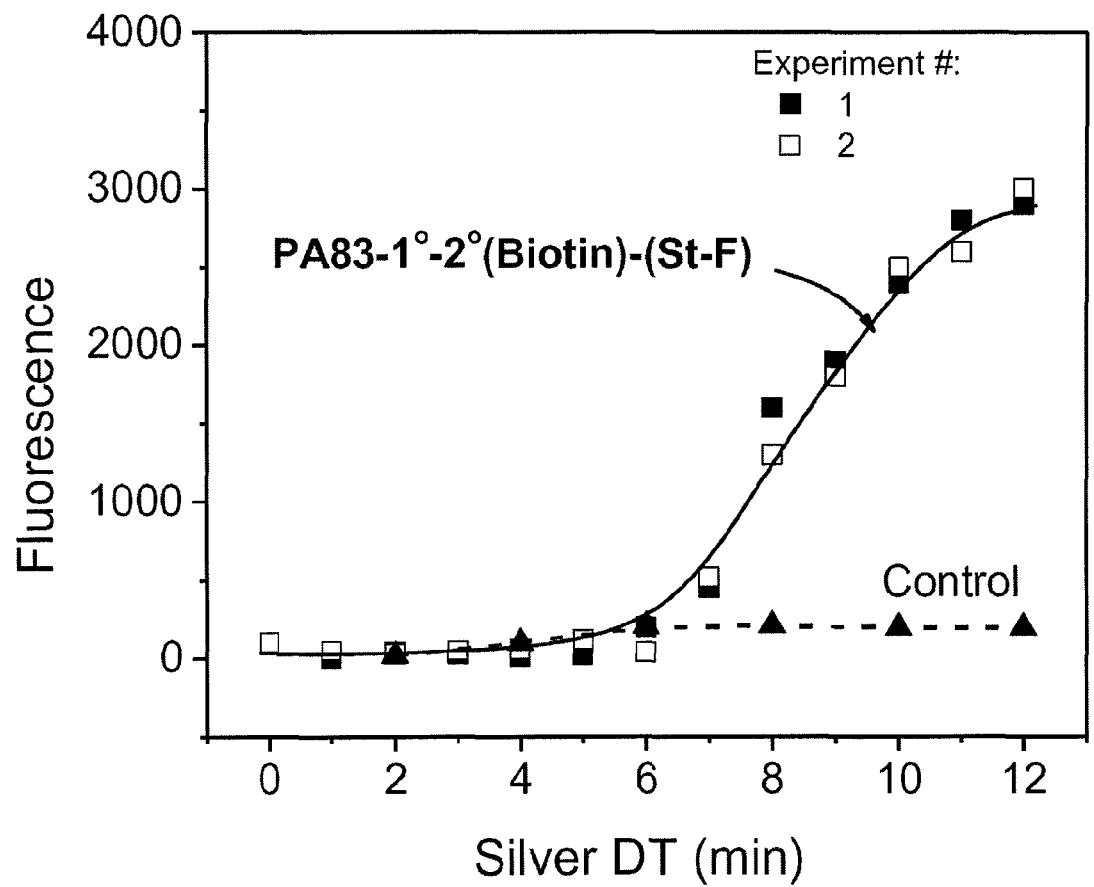
FIG. 4 shows the fluorescence of the chromophore (fluorescein), attached to the multiprotein complex within SiF wells, nonlinearly depends on silver DT. Loading of the PA protein and its detection, using primary (1) and secondary (2) biotinylated antibody and fluorescein-labeled streptavidin, was undertaken using an ELISA-like protocol (see protocol 1 in Materials and Methods). Control: streptavidin-fluorescein incubated for 10 min in SiF plate wells. Fluorescence excitation was undertaken using a 473-nm laser line, and emission was collected at 520 nm.

To study the effect of silver NPs on the fluorescence signal, the standard ELISA (see protocol 1 in Materials and Methods) was used based on a fluorescein-labeled streptaviding biotin system. FIG. 4 shows the dependence of the fluorescence signal on silver DT. At DT<6 min, the fluorescence signal is low and even decreases slightly with a reduction in DT. An increase at DT>7 min exhibits a sharp rise in fluorescence, which approaches saturation at DT>10 min. Interestingly, the dependences of the MEF effect on silver DT for fluorescein in solution and for that attached to the surface are similar (FIG. 3 [right panel] and FIG. 4), reflecting the generic near-field enhancing properties of MEF. In the case of fluorescein attached to the surface protein complex, the MEF effect shows strong dependence on the silver NPs' size and density, both of which increase on an increase in DT. In addition, the result shows that PA preferentially binds to the hydrophilic resin, which covers the well bottom, but not to the deposited SiFs. In this case, the deposition of NPs decreases the surface area available for PA binding. Subsequently, in the absence of a compensating strong MEF effect, one would expect this to lead to a decrease in the signal. To understand this change in MEF, which is known to depend strongly on near-field (electric field) distribution and intensity, theoretical FDTD simulations of the system were performed.

Figure 5:
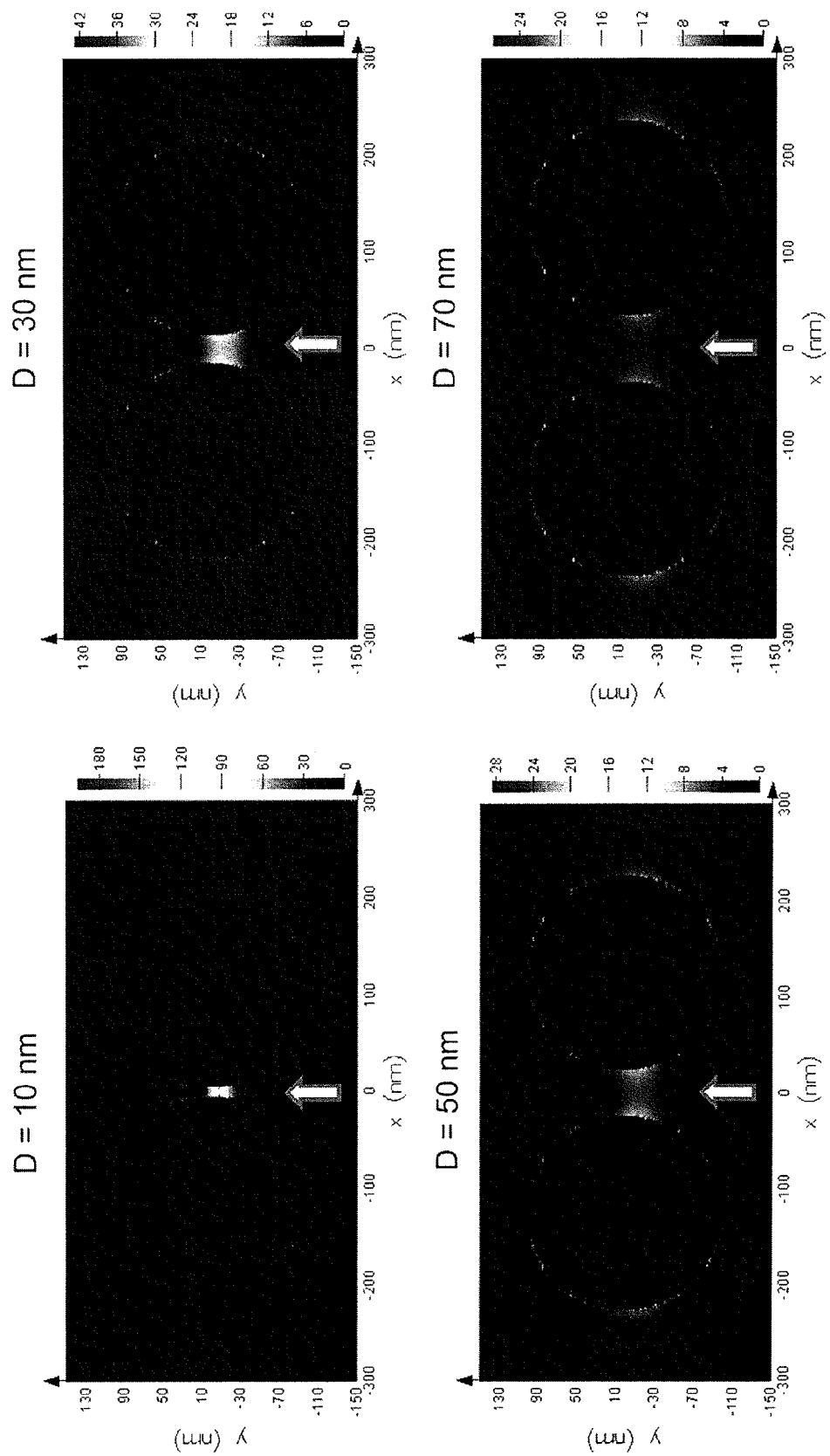
FIG. 5 shows FDTD simulations of the near field for the progressive change of SiF NPs' density (radius=100 nm). Two NPs are attached to the glass slide (a glass slide is on the top of the NPs); the white arrow shows the direction of the incident light (473 nm). The intensity of the near field increases from approximately 20 to 200 a.u. on a decrease in the interparticle distance (D). D is the distance between the surfaces of two silver NPs that changes on SiF DT.

FIG. 5 shows the results of FDTD simulations of the near field for the progressive change of SiFs' density on a glass surface, a model system for our wells. At large interparticle distance (low SiFs' density), the near-field intensity around NPs is low at approximately 20 a.u. (note that incident far-field intensity is an arbitrary 1.0). The intensity increases nearly 10-fold (the intensity of the near-field at D=10 nm is ~200 a.u.) on a decrease in the interparticle distance. A remarkable localized enhancement of the electric near field is a result of the resonance interaction between the plasmon systems of two adjacent silver NPs. The change in the near-field intensity is nonlinear, is observed only on quite short interparticle distances (<30 nm), and correlates well with the fluorescence enhancement shown in FIG. 4. In this case, the total enhancement of fluorescence could be considered as a superposition of at least two effects, enhanced absorption and enhanced emission: coupling of a dye with NP surface plasmons (i.e., resonance interaction between electronic systems of a chromophore and an NP) (enhanced emission) and the enhanced intensity of the near field between the NPs (i.e., the field that forms the spacial distribution of high-frequency energy in the interparticle space that interacts with oscillating electronic system of proximal chromophores [38]) (enhanced absorption). It should be noted that the role of the near-field intensity and spacial distribution (volume) in the MEF effect was recently theoretically postulated and experimentally verified by our laboratory [44].

Figure 6:
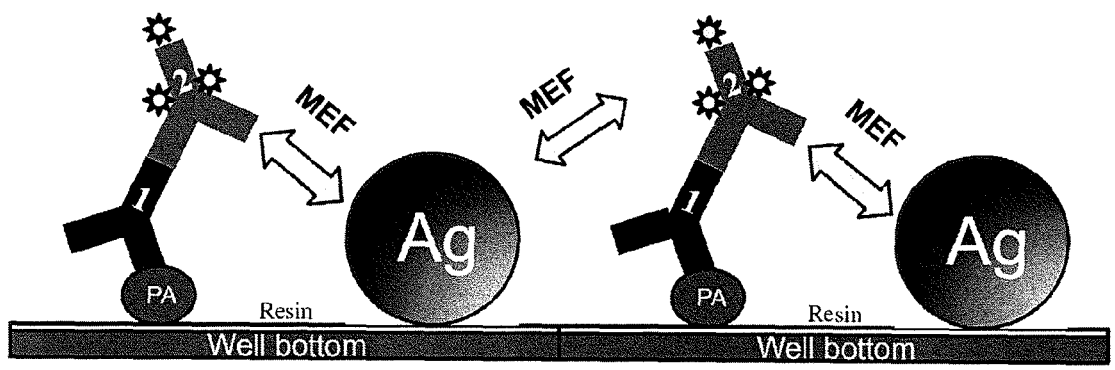
FIG. 6 shows the geometrical scheme of the MEF-PA assay. The multiprotein complex (PA, primary antibody, and secondary antibody labeled with fluorescein) is attached to the Immulon 4 HBX plate bottom resin. The MEF of fluorescein is induced by close proximity to the silver NPs deposited within wells and also depends on the size and density of SiFs.
Figure 7:
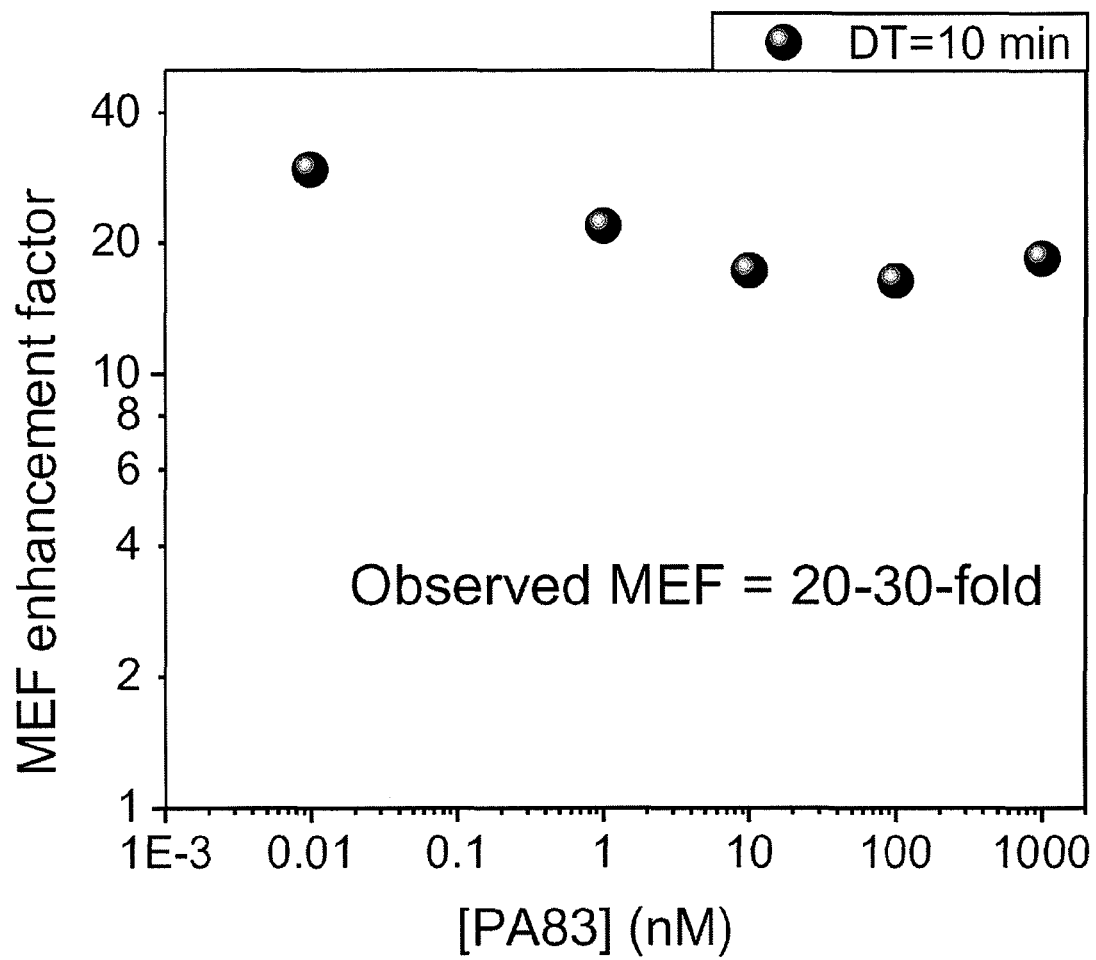
FIG. 7 shows the MEF effect observed for different loading concentrations of PA. MEF was measured as a ratio of the fluorescence intensity of the fluorescein-labeled PA antibody complex and measured in SiF plates to the observed fluorescence intensity from the control samples, that is, in original Immulon plates (no SiFs). Silver DT=10 min.

Based on these optimized surface properties for MEF, a MEF-PA assay system was proposed that is optimized for MEF as shown in FIG. 6 and showing the MEF of the PA-antibody-fluorescein system observed in SiF well plates. To characterize the magnitude of the MEF effect in SiF well plates for the MEF-PA assay, fluorescence signals from SiF plates and control plates were compared (i.e., plates containing no silver). FIG. 7 shows the MEF effect calculated as the ratio of the fluorescence signal of the fluorescein-labeled PA-antibody complex formed in SiF plates to the fluorescence signal from the control samples prepared in original nonsilvered Immulon plates. A decrease in the enhancement factor at larger loading concentrations of PA, >1 nM (>80 µg/ml), was evident and could be explained by self-quenching of the fluorophores due to fluorescence resonant energy transfer (homo-FRET) between identical labels. Homo-FRET increases with a decrease in the distance between fluorophores and, subsequently, with an increase in protein density on the surface.

The magnitude of the MEF effect for the limited range of loaded PA concentrations is approximately 20. This value of the MEF effect reflects the ratio of intensities measured from the surfaces (sample and control) of equal area (i.e., reflects not only the "real" MEF effect but also the difference in the amount of the labeled protein complexes attached to the surface). At silver DT=10 to 15 min, the approximate OD of SiF wells at 473 nm (wavelength of excitation) is 1.0 to 1.3. Assuming that the cross section of NP absorption is close to the NPs' size (diameter), one can estimate the fraction of NPs' free area as free=10-OD, which is approximately 5 to 10% of the total surface area. As shown herein, the PA protein binds preferentially to the hydrophilic surface of the well resin, and one can suggest that the amount of PA attached to the SiF surface is 10- to 20-fold less as compared with the nonsilvered surface. In that case, the observed MEF value can be corrected, which would correspond to an equal amount of dye-labeled complex on the surface. Subsequently, an enhancement factor in the range of 200- to 400-fold is estimated.

Characterization of the Ultra-Sensitive Rapid MEF-PA Assay

Figure 8:
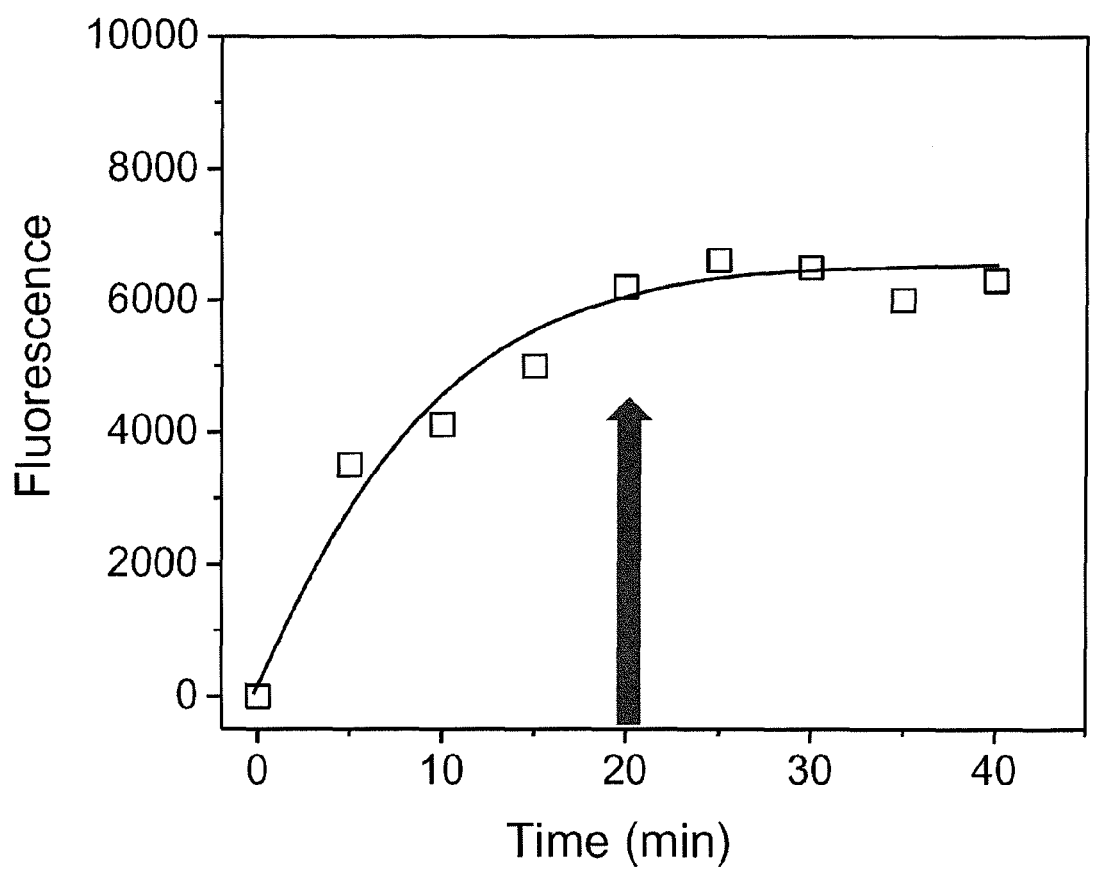
FIG. 8 shows the room temperature kinetics of PA attachment to the SiF well Immulon plate surface.

FIG. 8 demonstrates the kinetics of PA attachment to the Immulon plate wells covered with silver NPs. The incubation time of PA changed from 5 to 40 min, followed by washing the wells and then proceeding to follow protocol 2 (see Materials and Methods). The dependence of the fluorescence signal on incubation time shows that the attachment of PA to well bottoms approaches saturation at an incubation time longer than 20 min.

Figure 9:
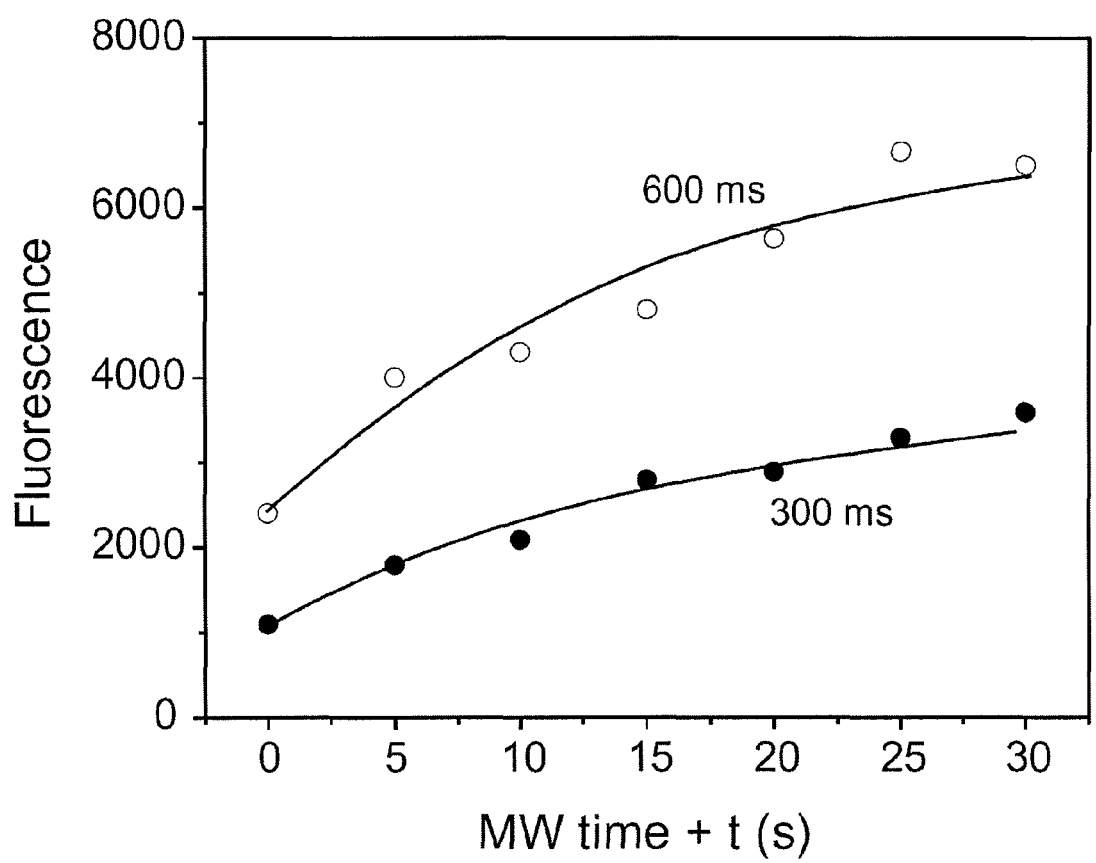
FIG. 9 shows the kinetics of the microwave-accelerated attachment of the PA protein to the plate well bottom. Microwave irradiation of PA in milk (milk/water=1:20), loaded onto SiF wells (Immulon), was undertaken for different irradiation times followed by treatment with blocking solution and antibodies (1 and 2-FITC). The fluorescence intensity was measured at two integration times: 300 and 600 ms. The lag time (t) between irradiation and fluorescence measurement was 1 to 2 min. The fluorescence signal from wells without PA was negligible.

Microwave irradiation (MW) of the plates filled with the PA solution significantly accelerates the protein absorption to the surface. FIG. 9 shows the kinetics of microwave-accelerated attachment of PA to the SiF wells. Measurements were undertaken at the same conditions as undertaken without MW, as shown in FIG. 8. The magnitude of the fluorescence signal collected from the wells reaches the same saturated value (F=6500 a.u.) but in 20 to 30 s (i.e., the process is accelerated ~60-fold as compared with non-MW conditions).

Figure 10:
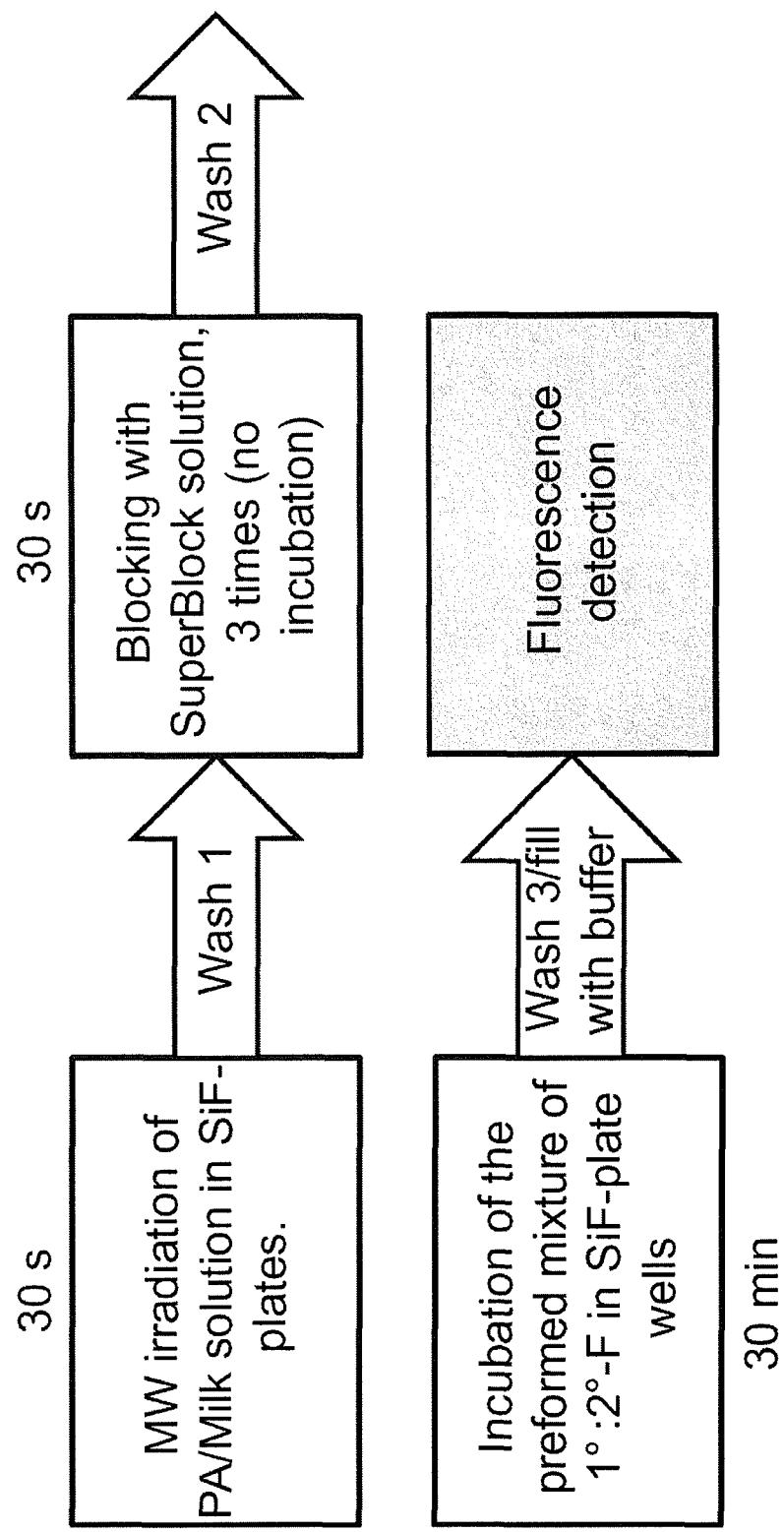
FIG. 10 shows the flow diagram of MEF-PA assay sequential procedures. 2°-F, secondary antibody labeled with fluorescein.
Figure 11:
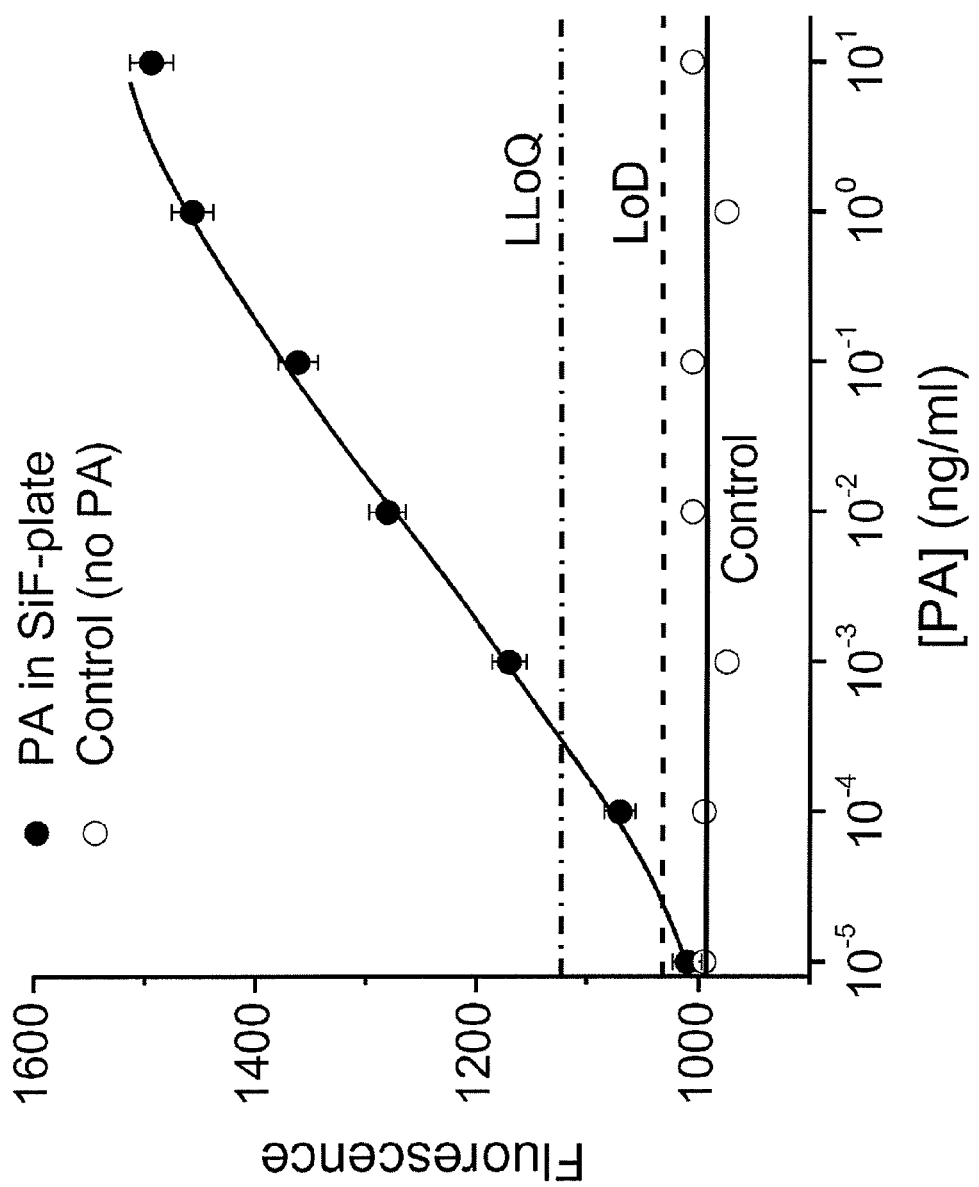
FIG. 11 shows the PA assay sensitivity curves measured in SiF plates. Fluorescence for the PA samples and control (no PA) was measured in SiF plates. LoD=mean fluorescence+3× standard deviation (dashed line); LLoQ=10× standard deviation (dashed-dotted line).

The flow diagram for the rapid MEF-PA assay protocol is shown in FIG. 10. The total time of the assay, including microwave-accelerated absorption of PA on the surface, is less than 40 min. Using this protocol, the MEF-PA assay sensitivity in the SiF plates was measured using different loading concentrations of PA (from 10 ng/ml to 0.01 pg/ml) and the control (no PA in the samples) (FIG. 11). The MEF-PA assay demonstrates extremely high sensitivity to PA—approaching the pg/ml level. Fluorescence readings from the plates can be reliably registered, even for the PA loading concentration of 0.1 pg/ml. The limit of detection (LoD) and lower limit of quantitation (LLoQ) for PA were calculated, wherein the LoD is 0.1 pg/ml and the LLoQ is 1 pg/ml. Taking into account that the loading volume of the PA solution (1 pg/ml) is 80 µl, one can estimate the number of protein molecules in one well as n=NA×[PA]×V=106, where NA is Avagadro's number. Consequently, the MEF-PA assay is sensitive to approximately 1 million PA molecules in our SiF plate well. This suggests that, as shown in FIG. 11, that the analytical sensitivity is better than 1 pg/ml.

The present invention provides for an ultra-sensitive and rapid MEF-PA assay based on both enhancement of the fluorescence signal by silver NPs (SiFs) and microwave-accelerated absorption of a protein onto a surface. This "rapid catch and signal" (RCS) technology can be used for not only the PA protein but can also be used for other protein antigens, as well as toxins, by simply changing the capture antibody. This system and method allows for detecting PA at high sensitivity in less than 40 min.

REFERENCES

The contents of all references cited herein are incorporated by reference herein for all purposes.

[1] R. Frank, R. Hargreaves, Clinical biomarkers in drug discovery and development, *Nat. Rev. Drug Discovery*, 2 (2003), pp. 566-580.

[2] P. C. Turnbull, Introduction: anthrax history, disease, and ecology, *Curr. Top. Microbiol. Immunol.*, 271 (2002), pp. 1-19.

[3] K. A. Edwards, H. A. Clancy, A. J. Baeumner, *Bacillus anthracis*: toxicology, epidemiology, and current rapid-detection methods, *Anal. Bioanal. Chem.*, 384 (2006), pp. 73-84.

[4] P. S. Brachman, Inhalation anthrax, *Ann. N.Y. Acad. Sci.*, 353 (1980), pp. 83-93.

[5] J. A. Jernigan, D. S. Stephens, D. A. Ashford, C. Omenaca, M. S. Topiel, M. Galbraith, M. Tapper, T. L. Fisk, S. Zaki, T. Popovic, R. F. Meyer, C. P. Quinn, S. A. Harper, S. K. Fridkin, J. J. Sejvar, C. W. Shepard, M. McConnell, J. Guarner, W. J. Shieh, J. M. Malecki, J. L. Gerberding, J. M. Hughes, B. A. Perkins, Bioterrorism-related inhalational anthrax: the first 10 cases reported in the United States, *Emerg. Infect. Dis.*, 7 (2001), pp. 933-944.

[6] H. Smith, J. Keppie, Observations on experimental anthrax: demonstration of a specific lethal factor produced in vivo by *Bacillus anthracis*, *Nature*, 173 (1954), pp. 869-870.

[7] H. Smith, J. Keppie, J. L. Stanley, P. W. Harris-Smith, The chemical basis of the virulence of *Bacillus anthracis*: IV. Secondary shock as the major factor in death of guinea pigs from anthrax, *Br. J. Exp. Pathol.*, 36 (1955), pp. 323-335.

[8] T. C. Dixon, M. Meselson, J. Guillemin, P. C. Hanna, Anthrax, *N. Engl. J. Med.*, 341 (1999), pp. 815-826.

[9] D. R. Franz, P. B. Jahrling, A. M. Friedlander, D. J. McClain, D. L. Hoover, W. R. Bryne, J. A. Pavlin, G. W. Christopher, E. M. Eitzen Jr., Clinical recognition and management of patients exposed to biological warfare agents, *JAMA*, 278 (1997), pp. 399-411.

[10] K. C. Brittingham, G. Ruthel, R. G. Panchal, C. L. Fuller, W. J. Ribot, T. A. Hoover, H. A. Young, A. O. Anderson, S. Bavari, Dendritic cells endocytose *Bacillus anthracis* spores: implications for anthrax pathogenesis, *J. Immunol.*, 174 (2005), pp. 5545-5552.

[11] A. Cleret, A. Quesnel-Hellmann, A. Vallon-Eberhard, B. Verrier, S. Jung, D. Vidal, J. Mathieu, J. N. Tournier, Lung dendritic cells rapidly mediate anthrax spore entry through the pulmonary route, *J. Immunol.*, 178 (2007), pp. 7994-8001.

[12] C. Guidi-Rontani, M. Levy, H. Ohayon, M. Mock, Fate of germinated *Bacillus anthracis* spores in primary murine macrophages, *Mol. Microbiol.,* 42 (2001), pp. 931-938.

[13] J. M. Ross, The pathogenesis of anthrax following the administration of spores by the respiratory route, *J. Pathol. Bacteriol.,* 73 (1957), pp. 485-494.

[14] J. Stephen, Anthrax toxin, F. Dorner, J. Drews (Eds.), Pharmacology of Bacterial Toxins, Pergamon, Oxford, UK (1986), pp. 381-395.

[15] K. R. Klimpel, S. S. Molloy, G. Thomas, S. H. Leppla, Anthrax toxin protective antigen is activated by a cell surface protease with the sequence specificity and catalytic properties of furin, *Proc. Natl. Acad. Sci. USA,* 89 (1992), pp. 10277-10281.

[16] J. Mogridge, K. Cunningham, R. J. Collier, Stoichiometry of anthrax toxin complexes, *Biochemistry,* 41 (2002), pp. 1079-1082.

[17] J. Mogridge, K. Cunningham, D. B. Lacy, M. Mourez, R. J. Collier, The lethal and edema factors of anthrax toxin bind only to oligomeric forms of the protective antigen, *Proc. Natl. Acad. Sci. USA,* 99 (2002), pp. 7045-7048.

[18] P. S. Brachman, A. Kaufman, Bacterial Infections of Humans: Epidemiology and Control, Plenum Medical, New York (1998).

[19] J. C. Milne, D. Furlong, P. C. Hanna, J. S. Wall, R. J. Collier, Anthrax protective antigen forms oligomers during intoxication of mammalian cells, *J. Biol. Chem.,* 269 (1994), pp. 20607-20612.

[20] B. E. Turk, Manipulation of host signalling pathways by anthrax toxins, Biochem. J., 402 (2007), pp. 405-417.

[21] M. N. Swartz, Recognition and management of anthrax—an update, *N. Engl. J. Med.,* 345 (2001), pp. 1621-1626.

[22] E. R. Swanson, D. E. Fosnocht, Anthrax threats: a report of two incidents from Salt Lake City, *J. Emerg. Med.,* 18 (2000), pp. 229-232.

[23] J. J. Walsh, N. Pesik, C. P. Quinn, V. Urdaneta, C. A. Dykewicz, A. E. Boyer, J. Guarner, P. Wilkins, K. J. Norville, J. R. Barr, S. R. Zaki, J. B. Patel, S. P. Reagan, J. L. Pirkle, T. A. Treadwell, N. R. Messonnier, L. D. Rotz, R. F. Meyer, D. S. Stephens, A case of naturally acquired inhalation anthrax: clinical care and analyses of anti-protective antigen immunoglobulin G and lethal factor, *Clin. Infect. Dis.,* 44 (2007), pp. 968-971.

[24] D. Kobiler, S. Weiss, H. Levy, M. Fisher, A. Mechaly, A. Pass, Z. Altboum, Protective antigen as a correlative marker for anthrax in animal models, *Infect. Immun.,* 74 (2006), pp. 5871-5876.

[25] R. Mabry, K. Brasky, R. Geiger, R. Carrion Jr., G. B. Hubbard, S. Leppla, J. L. Patterson, G. Georgiou, B. L. Iverson, Detection of anthrax toxin in the serum of animals infected with *Bacillus anthracis* by using engineered immunoassays, *Clin. Vaccine Immunol.,* 13 (2006), pp. 671-677.

[26] S. Tang, M. Moayeri, Z. Chen, H. Harma, J. Zhao, H. Hu, R. H. Purcell, S. H. Leppla, I. K. Hewlett, Detection of anthrax toxin by an ultrasensitive immunoassay using europium nanoparticles, *Clin. Vaccine Immunol.,* 16 (2009), pp. 408-413.

[27] M. Moayeri, J. F. Wiggins, S. H. Leppla, Anthrax protective antigen cleavage and clearance from the blood of mice and rats, *Infect. Immun.,* 75 (2007), pp. 5175-5184.

[28] R. E. Biagini, D. L. Sammons, J. P. Smith, E. H. Page, J. E. Snawder, C. A. Striley, B. A. MacKenzie, Determination of serum IgG antibodies to *Bacillus anthracis* protective antigen in environmental sampling workers using a fluorescent covalent microsphere immunoassay, *Occup. Environ. Med.,* 61 (2004), pp. 703-708.

[29] R. T. Cummings, S. P. Salowe, B. R. Cunningham, J. Wiltsie, Y. W. Park, L. M. Sonatore, D. Wisniewski, C. M. Douglas, J. D. Hermes, E. M. Scolnick, A peptide-based fluorescence resonance energy transfer assay for *Bacillus anthracis* lethal factor protease, Proc. Natl. Acad. Sci. USA, 99 (2002), pp. 6603-6606.

[30] T. N. Huan, T. Ganesh, S. H. Han, M. Y. Yoon, H. Chung, Sensitive detection of an anthrax biomarker using a glassy carbon electrode with a consecutively immobilized layer of polyaniline/carbon nanotube/peptide, *Biosens. Bioelectron.,* 26 (2011), pp. 4227-4230.

[31] A. E. Boyer, M. Gallegos-Candela, R. C. Lins, Z. Kuklenyik, A. Woolfitt, H. Moura, S. Kalb, C. P. Quinn, J. R. Barr, Quantitative mass spectrometry for bacterial protein toxins: a sensitive, specific, high-throughput tool for detection and diagnosis, *Molecules,* 16 (2011), pp. 2391-2413.

[32] K. Aslan, I. Gryczynski, J. Malicka, E. Matveeva, J. R. Lakowicz, C. D. Geddes, Metal-enhanced fluorescence. An emerging tool in biotechnology, *Curr. Opin. Biotechnol.,* 16 (2005), pp. 55-62.

[33] K. Aslan, C. D. Geddes, Microwave-accelerated metal-enhanced fluorescence. Platform technology for ultrafast and ultrabright assays, *Anal. Chem.,* 77 (2005), pp. 8057-8067.

[34] K. Aslan, C. D. Geddes, New tools for rapid clinical and bioagent diagnostics: microwaves and plasmonic nanostructures, *Analyst,* 133 (2008), pp. 1469-1480.

[35] K. Aslan, J. Huang, G. M. Wilson, C. D. Geddes, Metal-enhanced fluorescence-based RNA sensing, *J. Am. Chem. Soc.,* 128 (2006), pp. 4206-4207.

[36] K. Aslan, Y. X. Zhang, S. Hibbs, L. Baillie, M. J. R. Previte, C. D. Geddes, Microwave-accelerated metal-enhanced fluorescence. Application to detection of genomic and exosporium anthrax DNA in <30 s, *Analyst,* 132 (2007), pp. 1130-1138.

[37] A. I. Dragan, K. Golberg, A. Elbaz, R. Marks, Y. Zhang, C. D. Geddes, Two-color, 30-second microwave-accelerated metal-enhanced fluorescence DNA assays: a new rapid catch and signal (RCS) technology, *J. Immunol. Methods,* 366 (2010), pp. 1-7.

[38] C. D. Geddes (Ed.), Metal-Enhanced Fluorescence, John Wiley, Hoboken, N.J. (2010).

[39] C. D. Geddes, J. R. Lakowicz, Metal-enhanced fluorescence, *J. Fluoresc.,* 12 (2002), pp. 121-129.

[40] K. Aslan, P. Holley, C. D. Geddes, Microwave-accelerated metal-enhanced fluorescence (MAMEF) with silver colloids in 96-well plates: application to ultra fast and sensitive immunoassays, high throughput screening, and drug discovery, *J. Immunol. Methods,* 312 (2006), pp. 137-147.

[41] K. Aslan, C. D. Geddes, Microwave-accelerated metal-enhanced fluorescence (MAMEF): application to ultra fast and sensitive clinical assays, *J. Fluoresc.,* 16 (2006), pp. 3-8.

[42] M. T. Albrecht, H. Li, E. D. Williamson, C. S. LeButt, H. C. Flick-Smith, C. P. Quinn, H. Westra, D. Galloway, A. Mateczun, S. Goldman, H. Groen, L. W. Baillie, Human monoclonal antibodies against anthrax lethal factor and protective antigen act independently to protect against *Bacillus anthracis* infection and enhance endogenous immunity to anthrax, *Infect. Immun.,* 75 (2007), pp. 5425-5433.

[43] R. Pribik, A. I. Dragan, Y. Zhang, C. Gaydos, C. D. Geddes, Metal-enhanced fluorescence (MEF): physical characterization of silver island films and exploring sample geometries, *Chem. Phys. Lett.,* 478 (2009), pp. 70-74.

[44] A. I. Dragan, C. D. Geddes, Excitation volumetric effects (EVE) in metal-enhanced fluorescence, *Phys. Chem. Chem. Phys.,* 13 (2011), pp. 3831-3838.

[45] R. P. Huang, Detection of multiple proteins in an antibody-based protein microarray system, *J. Immunol. Methods,* 255 (2001), pp. 1-13.

[46] Yang B, Sayers S, Xiang Z, He Y. Protegen: a web-based protective antigen database and analysis system. *Nucleic Acids Research.* 2011, Vol. 39, Database issue D1073-D1078.

[47] He Y, Xiang Z. Bioinformatics analysis of bacterial protective antigens in manually curated Protegen database. *Procedia in Vaccinology.* 2012. Volume 6. Pages 3-9.

That which is claimed is:

1. A method for detecting a target protein in a testing sample, the method comprising:
    a) providing a system comprising
        a substrate surface comprising immobilized metallic particles,
        wherein the metallic particles have a diameter from about 40 nm to about 120 nm and separated from each other with a distance from about 10 nm to 50 nm;
    b) introducing the testing sample to the substrate surface for a sufficient time and under conditions wherein the target protein in the testing sample binds to the substrate surface between the metallic particles and not to the metallic particles;
    c) introducing a first antibody having affinity for the target protein under conditions sufficient for the binding of the first antibody to form a target protein/first antibody complex and applying microwave energy in an amount sufficient to increase the binding of the first antibody to the target protein;
    d) introducing a second antibody having affinity for the first antibody, wherein the second antibody comprises at least one excitable molecule, wherein the excitable molecule is selected from the group of an intrinsic fluorophore, extrinsic fluorophore, and fluorescent dye, wherein binding to the first antibody positions the excitable molecule from about 5 nm to about 30 nm from at least one metallic particle;
    e) applying electromagnetic energy in an amount sufficient to excite the excitable molecule; and
    f) measuring the emissions from the excitable molecule and/or metallic particles to determine the existence of any target protein in the testing sample.

2. The method of claim 1, wherein the microwave energy is applied simultaneously during the introducing of the first antibody.

3. The method of claim 1, wherein the metallic particles have an elliptical, spherical, triangular or rod-like shape.

4. The method of claim 1, wherein the metallic particles are separated from each other by about 10 nm to about 30 nm.

5. The method of claim 1, wherein the excitable molecule is positioned from about 5 nm to about 20 nm from at least one metallic particle.

6. The method of claim 1, wherein the target protein in the testing sample is protective antigen PA83 of anthrax.

7. The method of claim 1, wherein the metallic particles are fabricated from Silver, Gold, Copper, Aluminum, Zinc, Nickel, Palladium, Tungsten, Platinum, Germanium, Indium, Iron, Tin, Rhodium or combinations thereof.

8. The method of claim 1, wherein the microwave radiation is applied in a frequency range from about 1 GHz to about 3 GHz with a power level in a range between about 100 watts and 700 watts.

\* \* \* \* \*